United States Patent
Je et al.

(10) Patent No.: US 8,541,113 B2
(45) Date of Patent: Sep. 24, 2013

(54) PYRENE COMPOUNDS AND ORGANIC ELECTROLUMINESCENT DEVICES USING THE SAME

(75) Inventors: Jong-Tae Je, Chungcheongbuk-do (KR); Se-jin Lee, Daejeon (KR); Bo-Kyoung Song, Chungcheonbuk-do (KR); Sang-Hae Lee, Daejeon (KR); Jin-Woo Park, Gyeongsangnam-do (KR)

(73) Assignee: SFC Co., Ltd., Cheongwon-kun, Chungcheongbuk-do (KR)

( * ) Notice: Subject to any disclaimer, the term of this patent is extended or adjusted under 35 U.S.C. 154(b) by 861 days.

(21) Appl. No.: 12/545,301

(22) Filed: Aug. 21, 2009

(65) Prior Publication Data
US 2010/0052526 A1    Mar. 4, 2010

(30) Foreign Application Priority Data

Aug. 26, 2008   (KR) .................. 10-2008-0083442
Jul. 22, 2009   (KR) .................. 10-2009-0066815

(51) Int. Cl.
| H01L 51/54 | (2006.01) |
| C07C 211/61 | (2006.01) |
| C07D 401/12 | (2006.01) |
| C07D 403/12 | (2006.01) |

(52) U.S. Cl.
USPC ........... 428/690; 313/504; 428/917; 546/111; 546/160; 546/264; 548/440; 564/426; 564/429

(58) Field of Classification Search
None
See application file for complete search history.

(56) References Cited

U.S. PATENT DOCUMENTS

| 7,053,255 B2 | 5/2006 | Ikeda et al. | |
| 7,233,019 B2 | 6/2007 | Ionkin et al. | |
| 7,571,894 B2 | 8/2009 | Sotoyama | |
| 7,927,716 B2 | 4/2011 | Matsuura et al. | |
| 8,012,609 B2 * | 9/2011 | Takeda .......................... | 428/690 |
| 2004/0137270 A1 * | 7/2004 | Seo et al. ....................... | 428/690 |
| 2004/0263067 A1 * | 12/2004 | Saitoh et al. .................. | 313/504 |
| 2005/0095459 A1 * | 5/2005 | Chin et al. ..................... | 428/690 |
| 2007/0009758 A1 | 1/2007 | Funahashi | |
| 2007/0063638 A1 * | 3/2007 | Tokairin et al. ............... | 313/504 |

FOREIGN PATENT DOCUMENTS

| KR | 10-2004-0057862 A | 7/2004 |
| KR | 10-2005-0107809 A | 11/2005 |
| WO | WO 2007/108666 A1 | 9/2007 |

* cited by examiner

*Primary Examiner* — Dawn Garrett
(74) *Attorney, Agent, or Firm* — Alston & Bird LLP

(57) ABSTRACT

A pyrene compound is provided. The pyrene compound is represented by Formula 1:

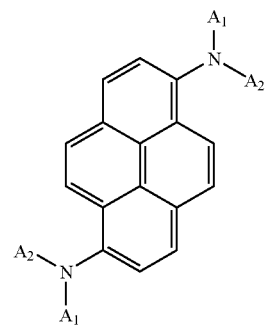

(1)

wherein $A_1$ and $A_2$ are as defined in the specification. Further provided is an organic electroluminescent device using the pyrene compound. The organic electroluminescent device has high color purity of blue light and shows long life characteristics. Therefore, the organic electroluminescent device is suitable for use in displays and lighting systems.

8 Claims, 3 Drawing Sheets

PYRENE COMPOUNDS AND ORGANIC ELECTROLUMINESCENT DEVICES USING THE SAME

CROSS REFERENCE TO RELATED APPLICATIONS

This application claims priority to Korean Patent Application No. 10-2008-0083442, filed Aug. 26, 2008, and Korean Patent Application No. 10-2009-0066815, filed Jul. 22, 2009, both of which are incorporated herein by reference in their entirety.

BACKGROUND OF THE INVENTION

1. Field of the Invention

The present invention relates to pyrene compounds and organic electroluminescent devices using the same. More specifically, the present invention relates to blue light emitting pyrene compounds with high color purity and long lifetime, and organic electroluminescent devices using the pyrene compounds.

2. Description of the Related Art

As displays have become larger in size in recent years, there has been an increasing demand for flat panel display devices that take up little space. Liquid crystal display devices as typical flat panel display devices can be reduced in weight when compared to the prior art cathode ray tubes (CRTs), but have disadvantages in that the viewing angle is limited, the use of backlight is inevitably required, etc. Organic light-emitting diodes, (OLEDs) as a new type of flat panel display devices are self-luminous display devices. Organic light-emitting diodes have the advantages of large viewing angle, light weight, small thickness, small size and short response time over liquid crystal display devices. Based on these advantages, the applicability of organic light-emitting diodes to full-color displays or lighting systems is expected. Under these circumstances, there is a growing need for blue light emitting materials with high luminance, high efficiency and high color purity.

U.S. Pat. No. 7,053,255 discloses a blue light emitting compound which has a diphenylanthracene structure at the center and a specific structure substituted with an aryl group at end portions, and an organic electroluminescence device using the blue light-emitting compound. This organic electroluminescent device has the drawbacks of insufficient efficiency of light emission and low luminance.

Further, U.S. Pat. No. 7,233,019 and Korean Unexamined Patent Publication No. 2006-0006760 disclose organic electroluminescent devices using substituted pyrene compounds. The devices have poor color purity of blue light, which makes it difficult to achieve deep blue light emission. Accordingly, there is a limitation in manufacturing displays providing a full range of natural colors.

SUMMARY OF THE INVENTION

It is a first object of the present invention to provide pyrene compounds with high color purity of blue light and long lifetime.

It is a second object of the present invention to provide organic electroluminescent devices using the pyrene compounds.

To accomplish the first object of the present invention, there is provided a pyrene compound represented by Formula 1:

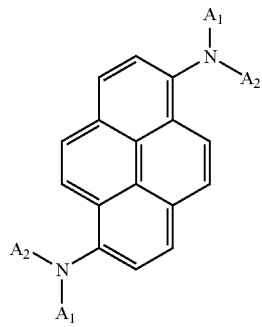

(1)

wherein $A_1$ and $A_2$ are each independently a $C_6$-$C_{24}$ aryl or $C_2$-$C_{24}$ heteroaryl group which is unsubstituted or substituted with at least one substituent selected from the group consisting of substituted $C_1$-$C_{24}$ alkyl groups, unsubstituted $C_1$-$C_{24}$ alkyl groups, substituted $C_3$-$C_{24}$ cycloalkyl groups, unsubstituted $C_3$-$C_{24}$ cycloalkyl groups, substituted $C_1$-$C_{24}$ alkoxy groups, unsubstituted $C_1$-$C_{24}$ alkoxy groups, cyano groups, halogen groups, substituted $C_6$-$C_{24}$ aryl groups, unsubstituted $C_6$-$C_{24}$ aryl groups, substituted $C_6$-$C_{24}$ aryloxy groups, unsubstituted $C_6$-$C_{24}$ aryloxy groups, substituted $C_2$-$C_{24}$ heteroaryl groups, unsubstituted $C_2$-$C_{24}$ heteroaryl groups, substituted $C_6$-$C_{40}$ arylamino groups, unsubstituted $C_6$-$C_{40}$ arylamino groups, substituted $C_2$-$C_{40}$ alkylamino groups, unsubstituted $C_2$-$C_{40}$ alkylamino groups, germanium, boron, substituted $C_1$-$C_{24}$ alkylsilyl groups, unsubstituted $C_1$-$C_{24}$ alkylsilyl groups, substituted $C_1$-$C_{24}$ arylsilyl groups, unsubstituted $C_1$-$C_{24}$ arylsilyl groups, and deuterium, with the proviso that the pyrene compound contains at least one deuterium atom and at least one halogen atom.

In a preferred embodiment, $A_1$ or $A_2$ is substituted or unsubstituted phenyl, substituted or unsubstituted naphthyl, substituted or unsubstituted pyridinyl, phenanthryl, substituted or unsubstituted biphenyl or substituted or unsubstituted terphenyl.

In a preferred embodiment, the substitutent of $A_1$ or $A_2$ contains at least one halogen atom. In a more preferred embodiment, the halogen atom is a fluorine atom (F).

In an embodiment, the pyrene compound may be selected from the group consisting of, but not limited to, the compounds represented by Formulas BD1 to BD89:

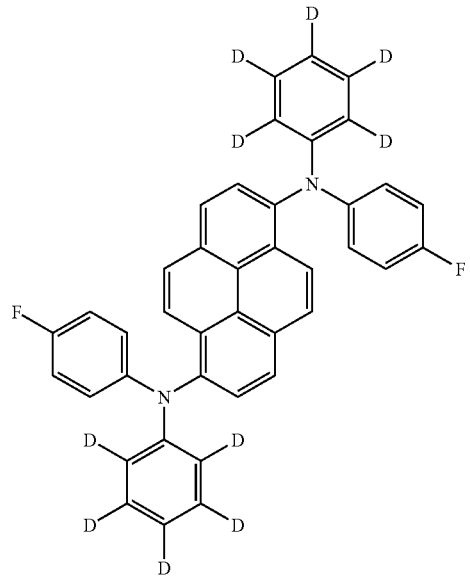

BD1

BD2
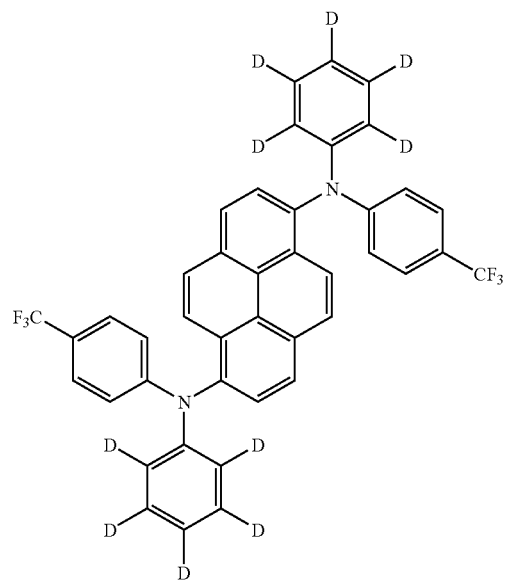
BD4
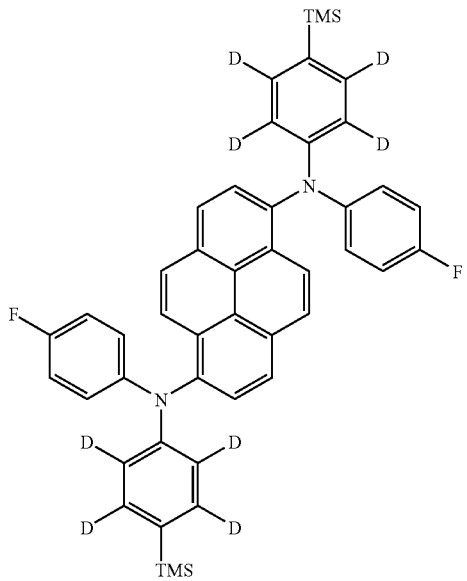
BD3
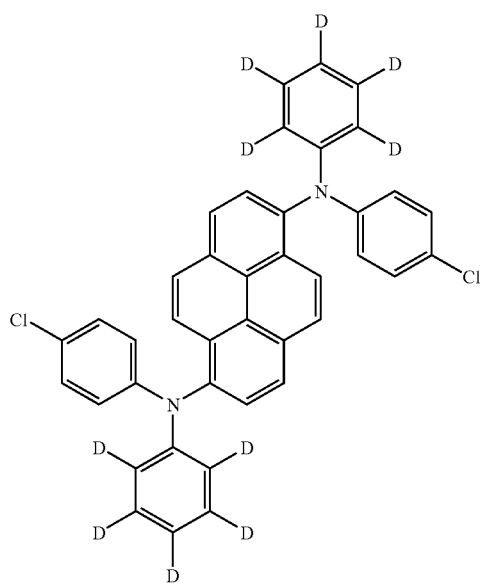
BD5
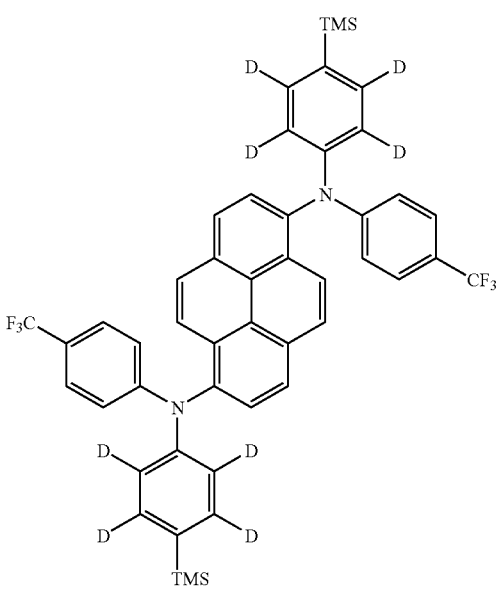

BD6
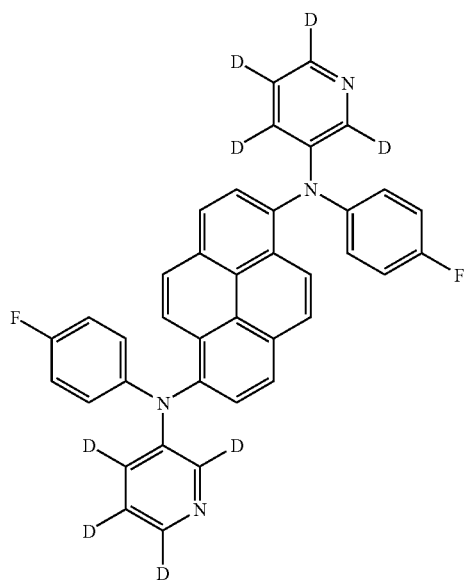
BD8
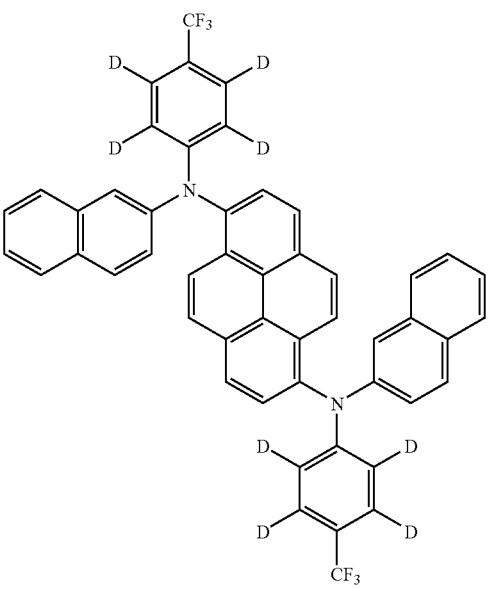
BD7
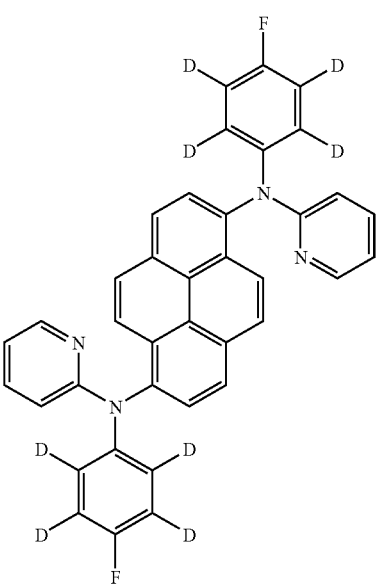
BD9

BD10
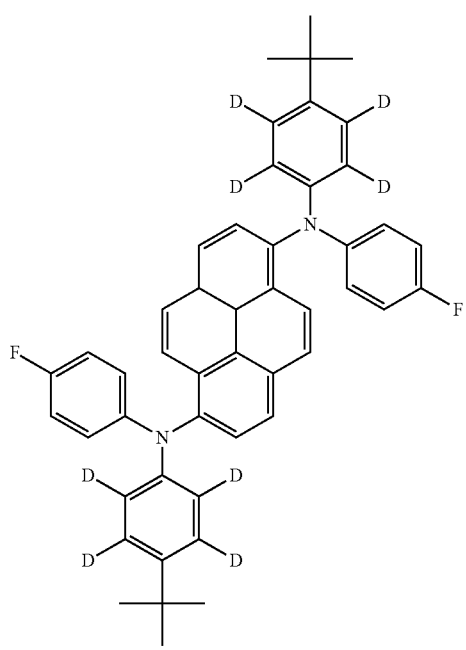
BD11
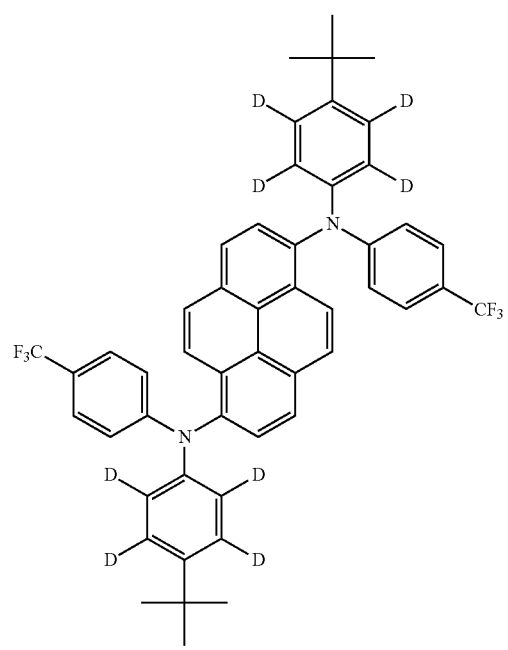
BD12
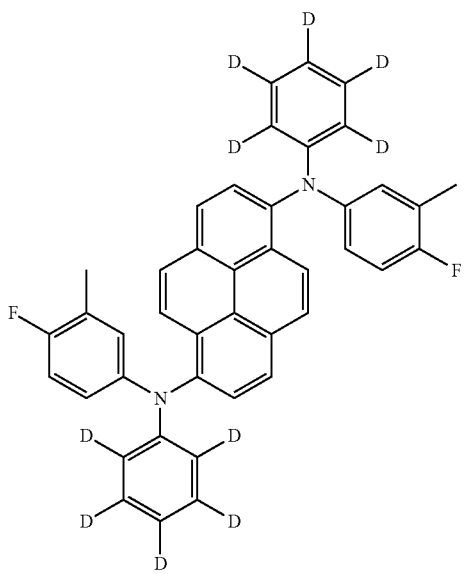
BD13
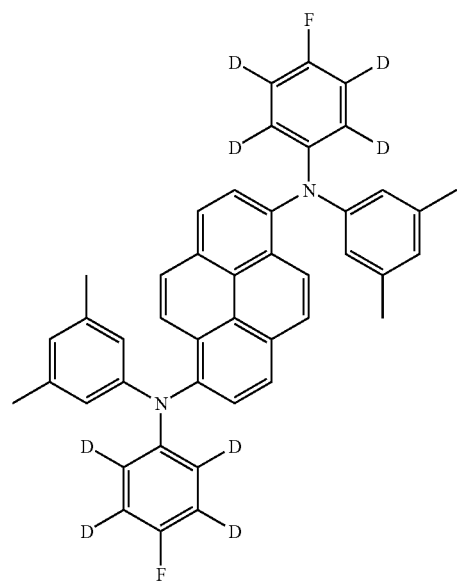

BD14
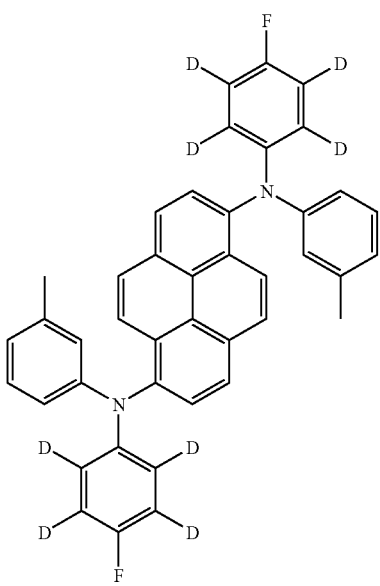
BD16
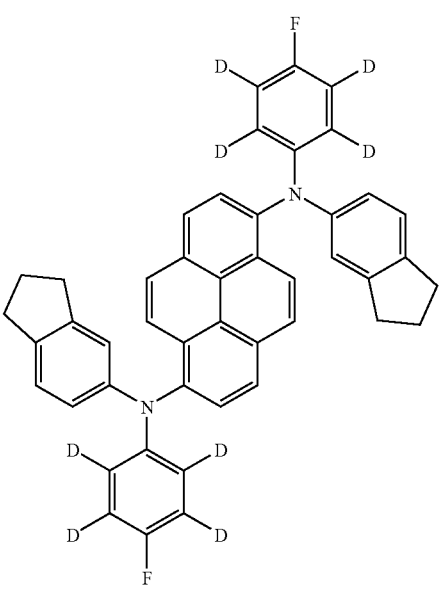
BD15
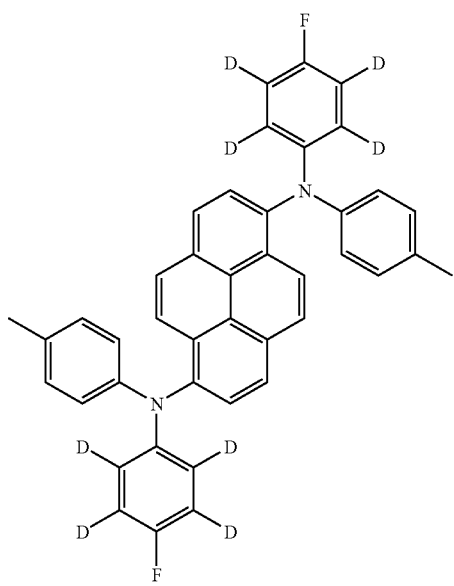
BD17
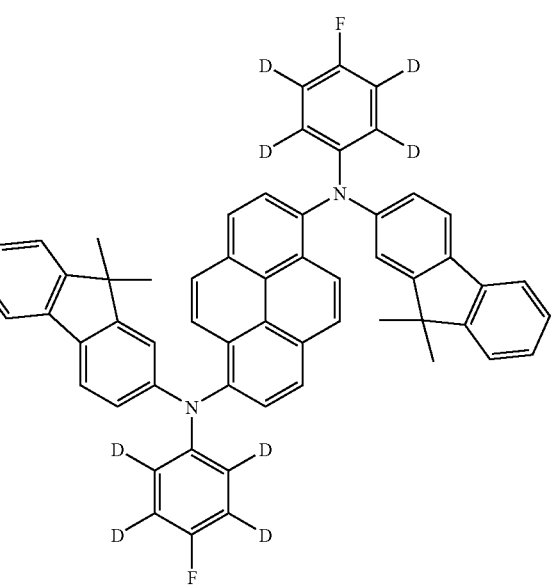

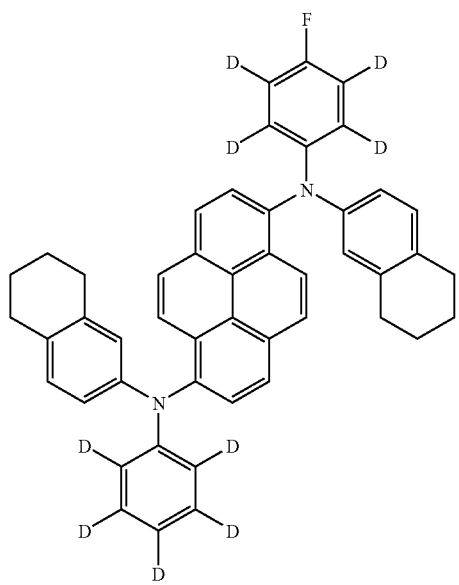
BD18
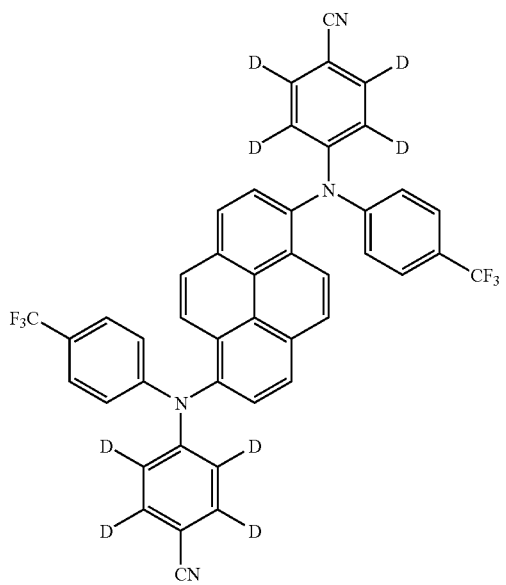
BD20
BD19
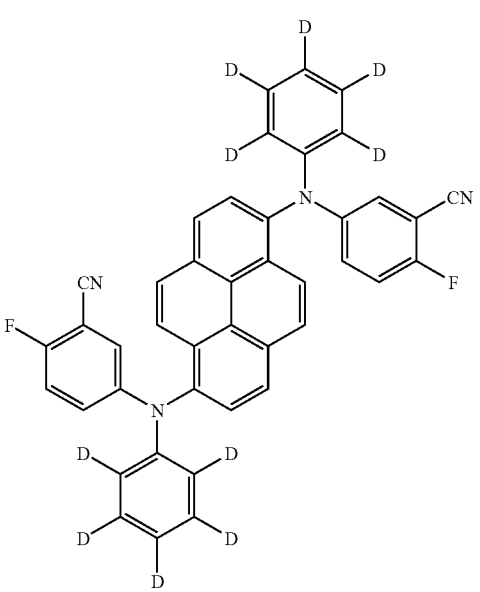
BD21

BD22
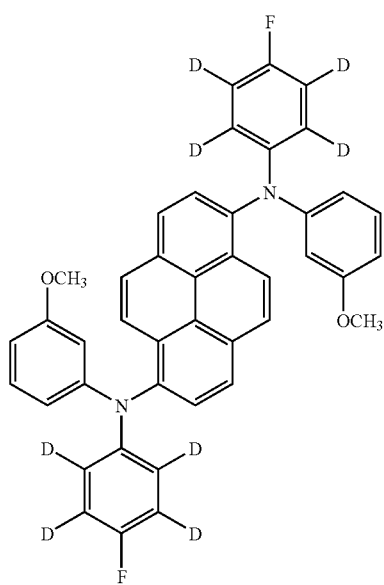
BD23
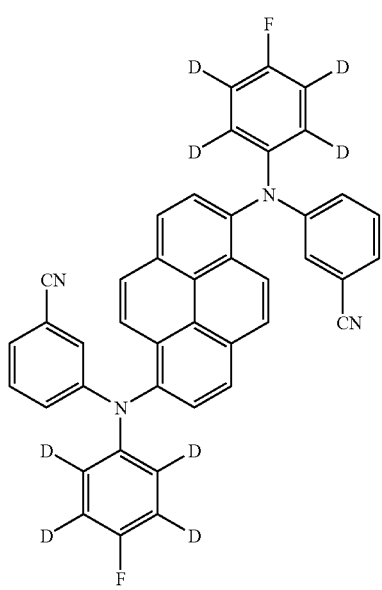
BD24
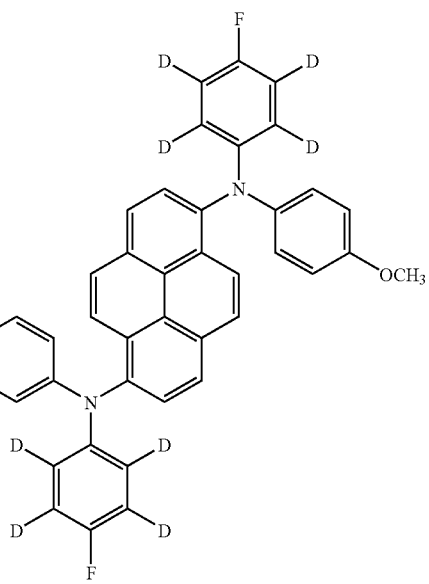
BD25
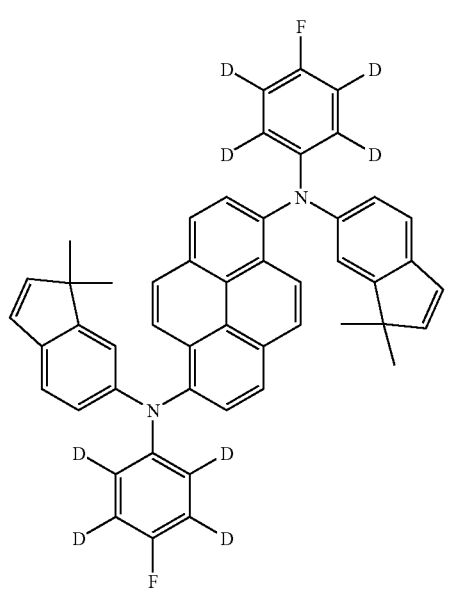

-continued
BD26
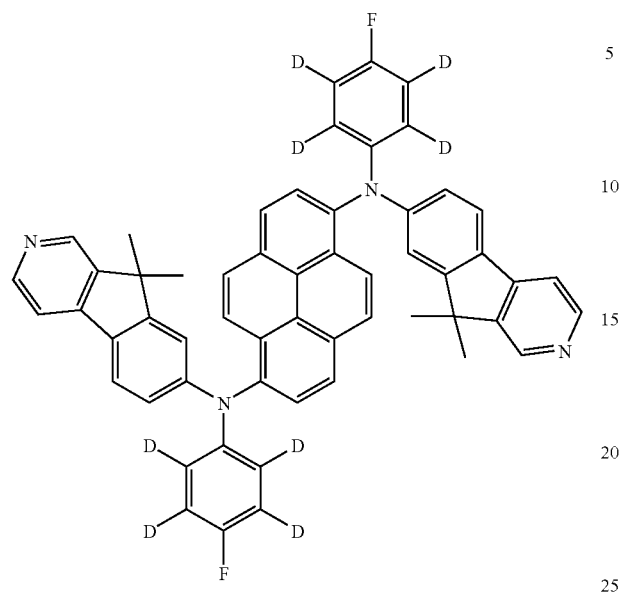
BD28
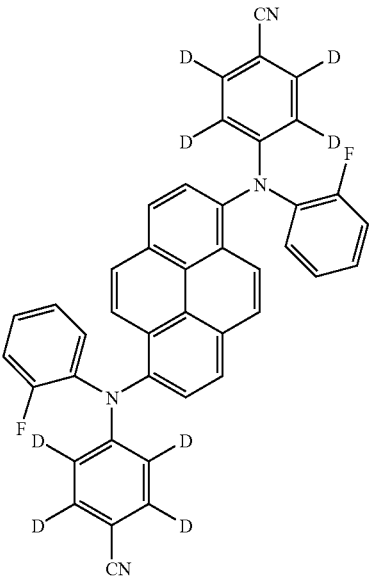
BD27
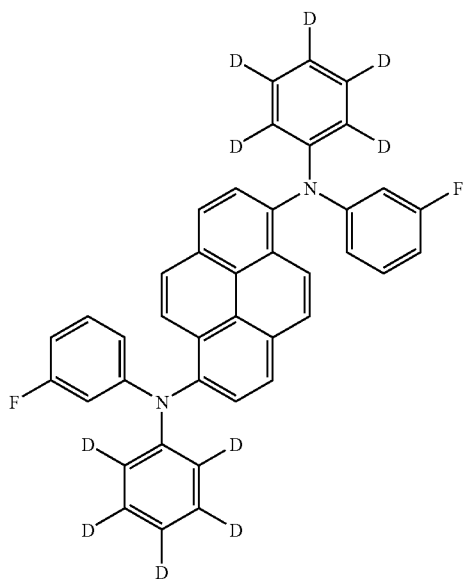
BD29
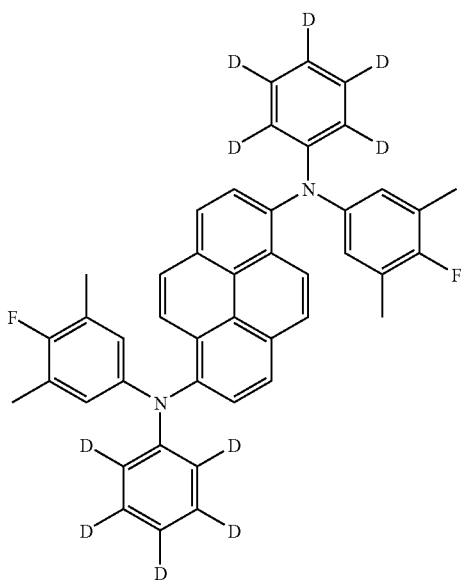

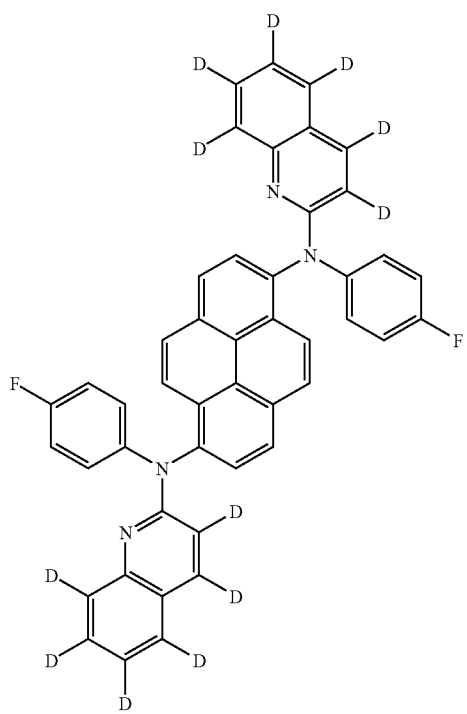
BD30
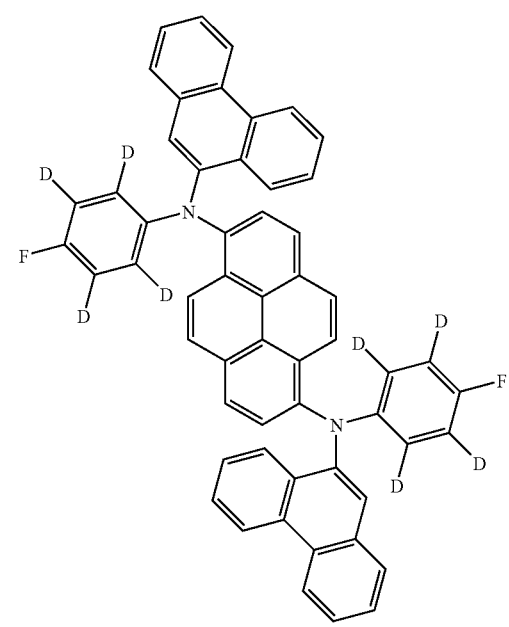
BD32
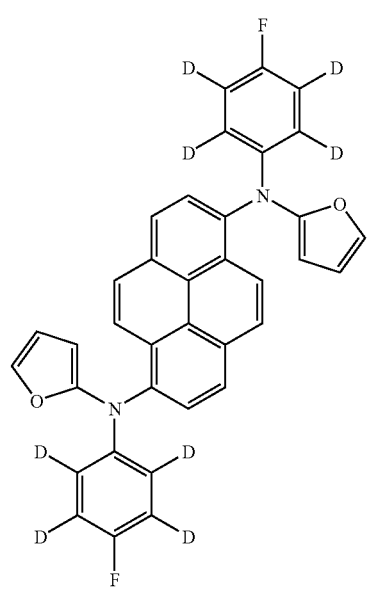
BD31
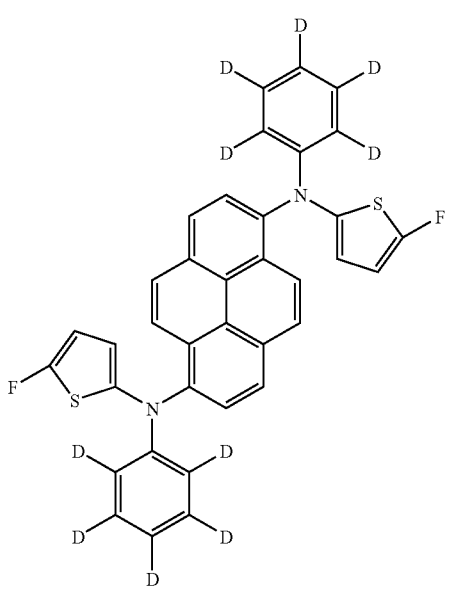
BD33

BD34
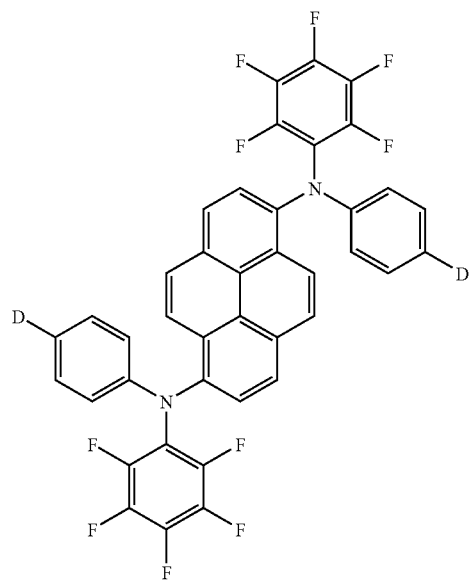
BD35
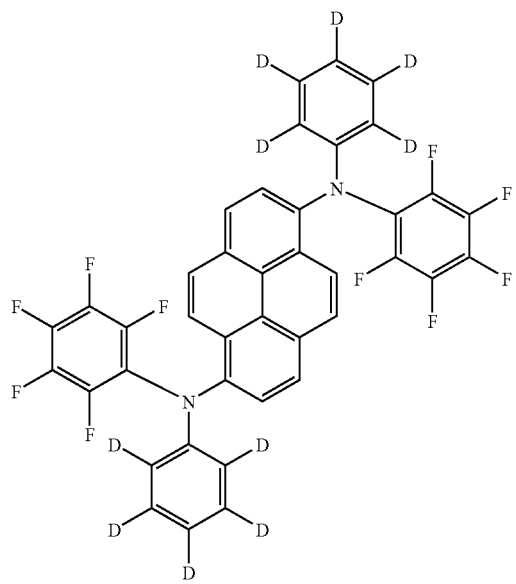
BD36
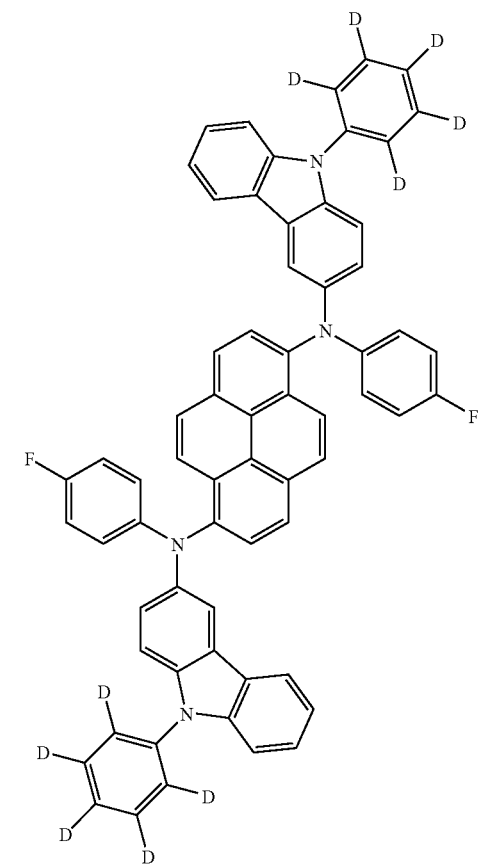
BD37
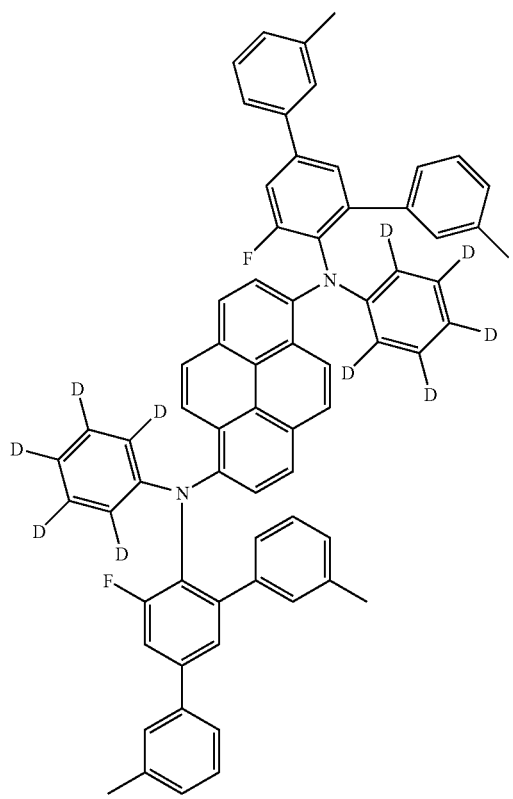

BD38
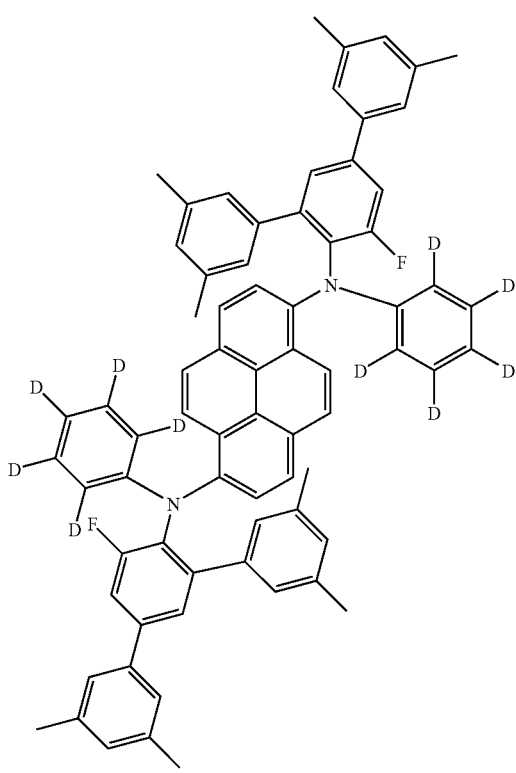
BD39
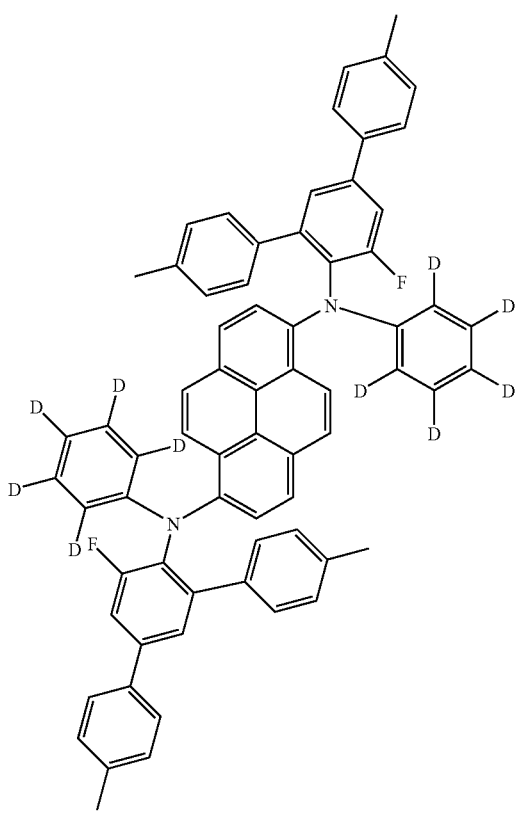
BD40
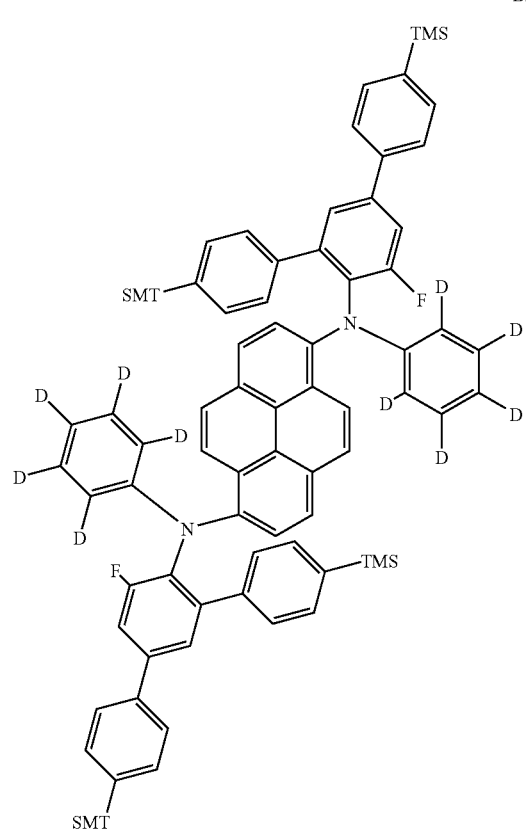
BD41
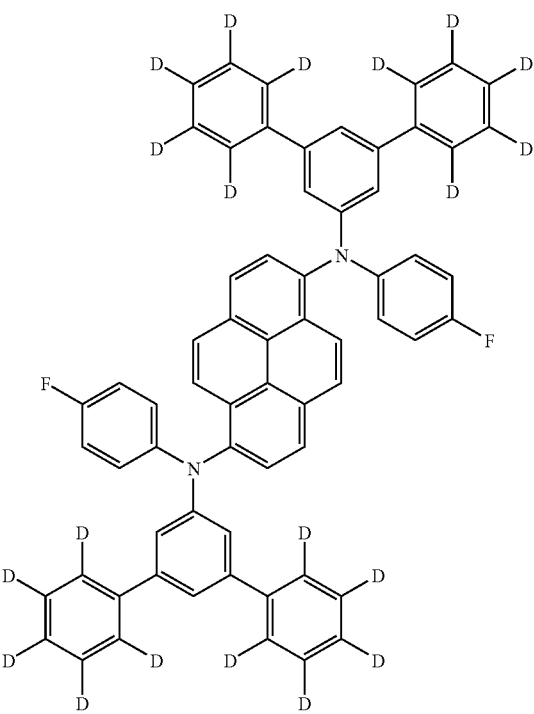

BD42
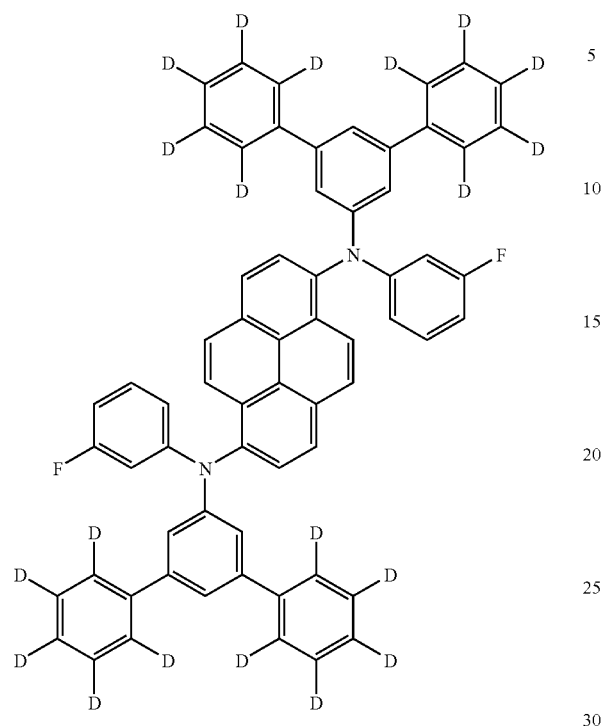
BD44
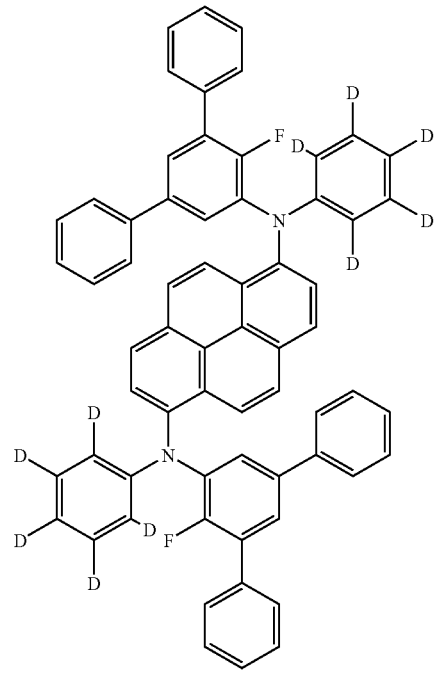
BD43
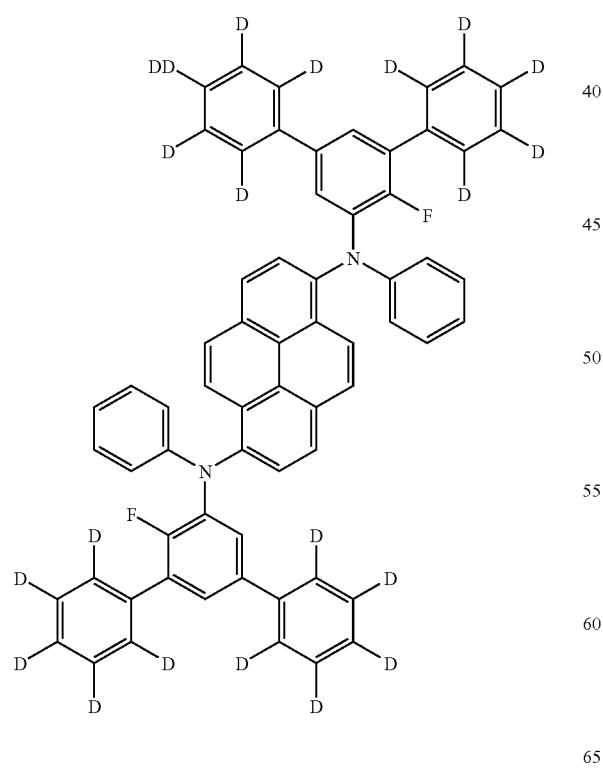
BD45
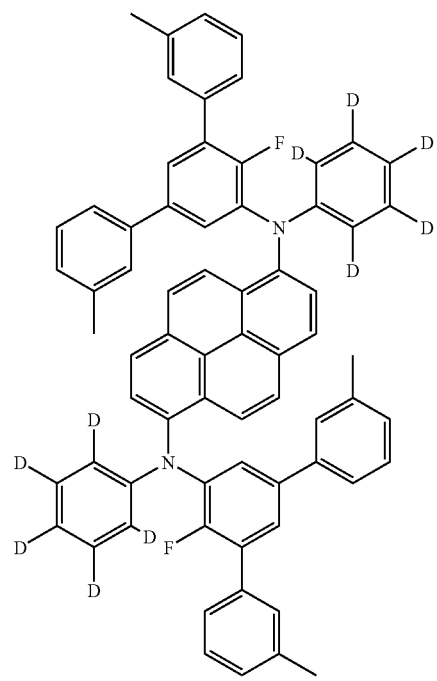

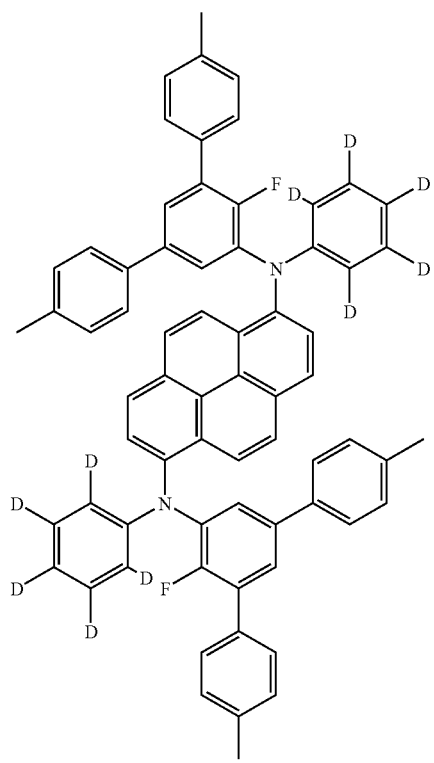
BD46
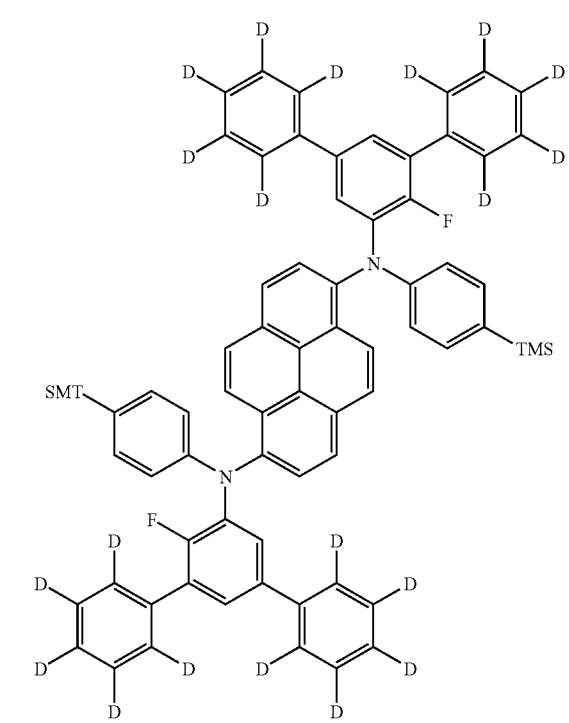
BD48
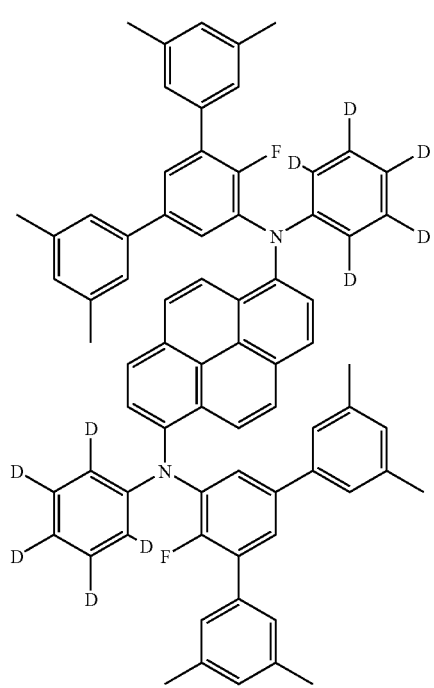
BD47
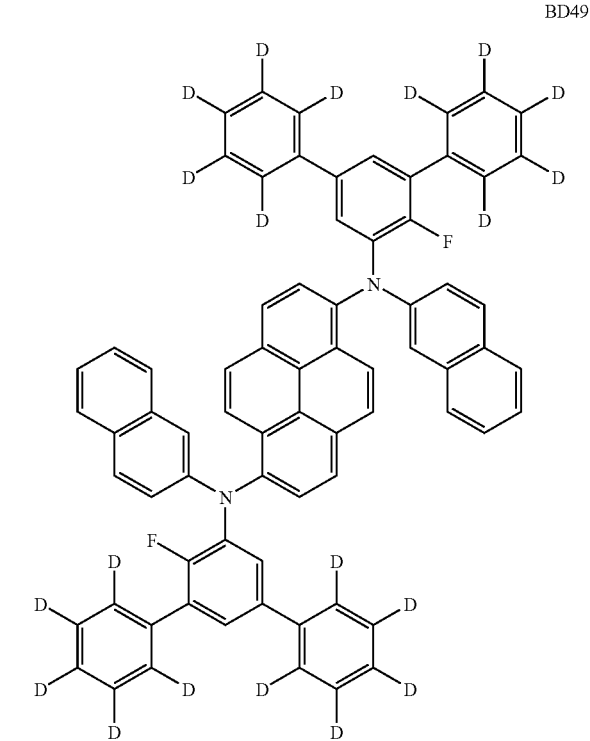
BD49

BD50
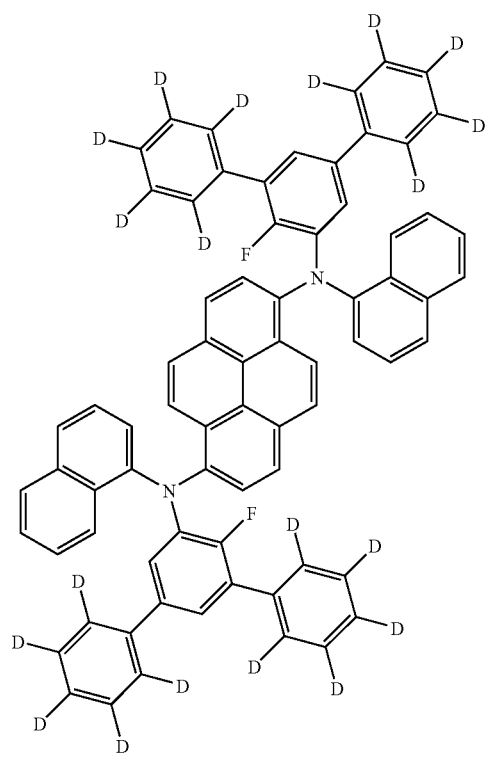
BD52
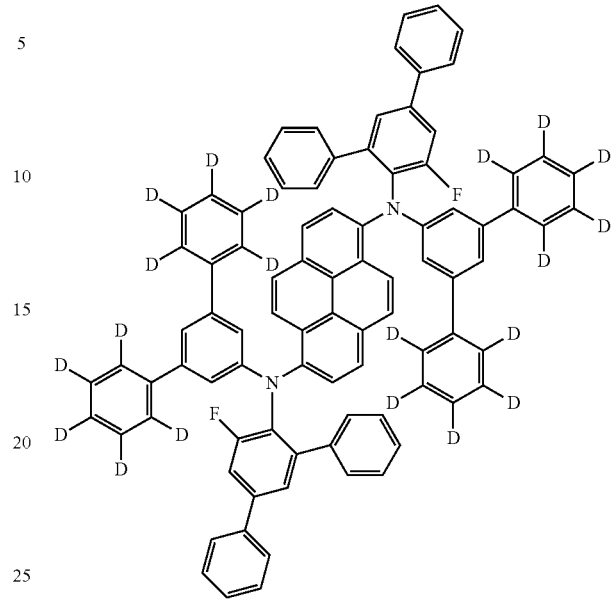
BD51
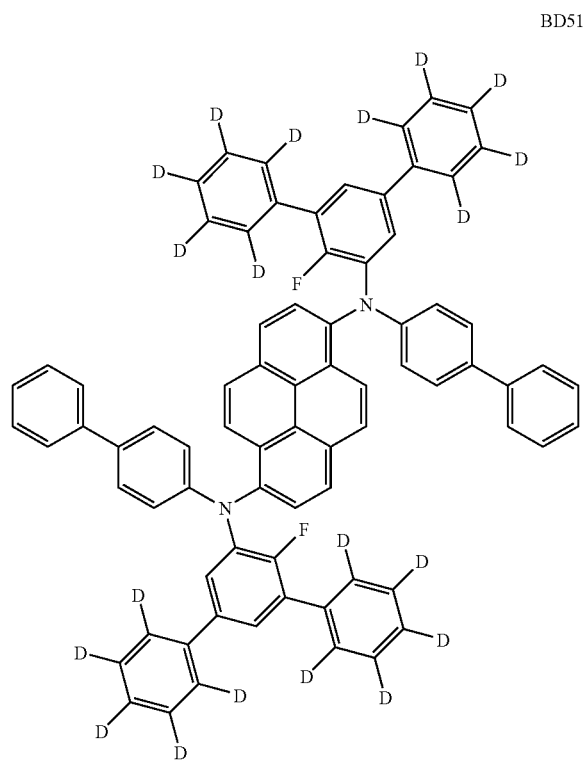
BD53
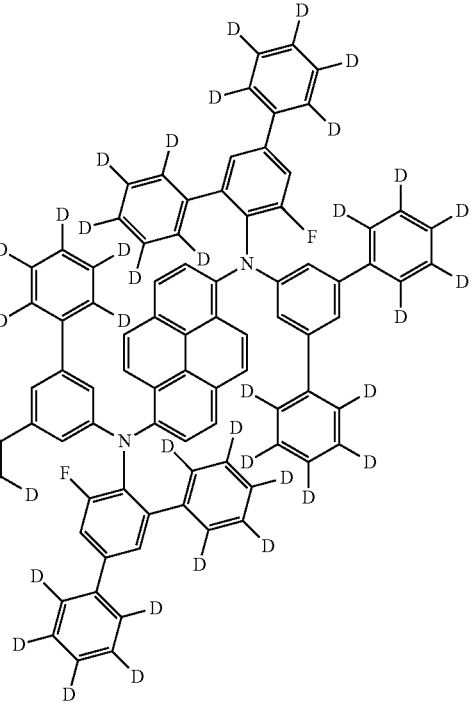

BD54
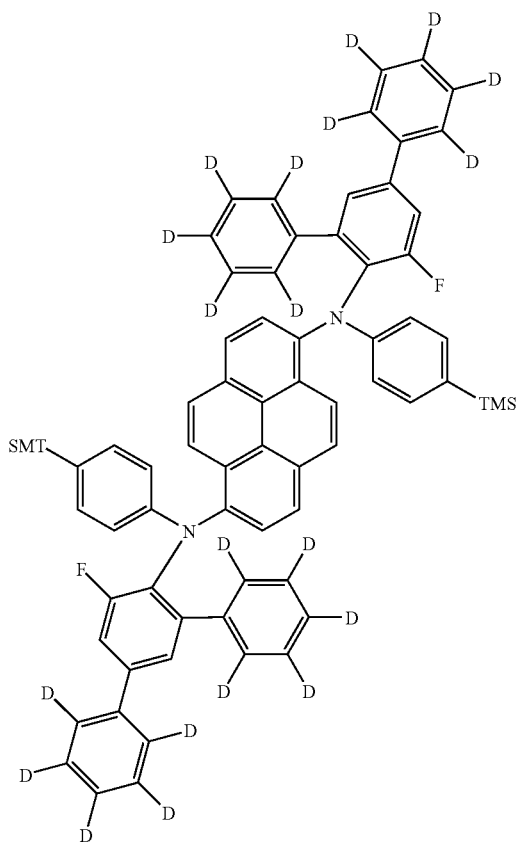
BD56
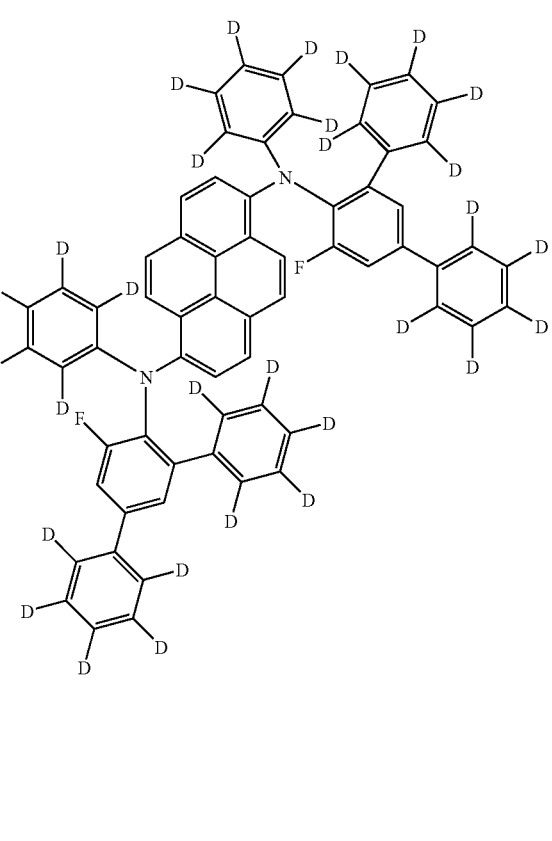
BD55
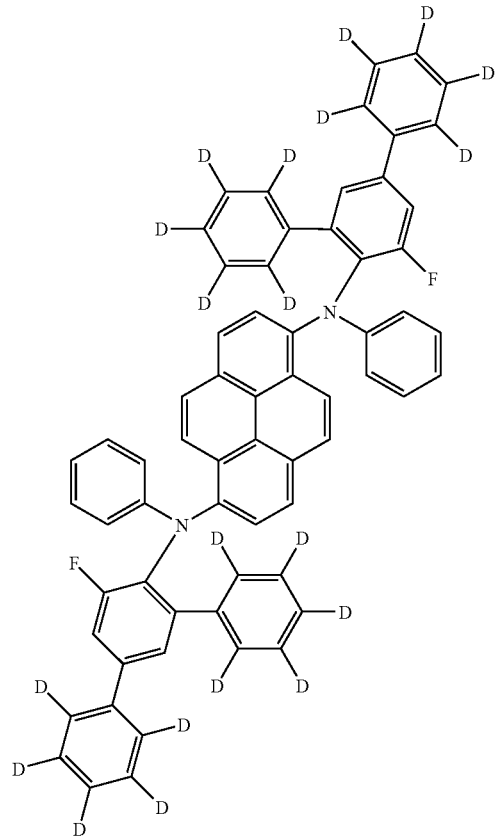
BD57
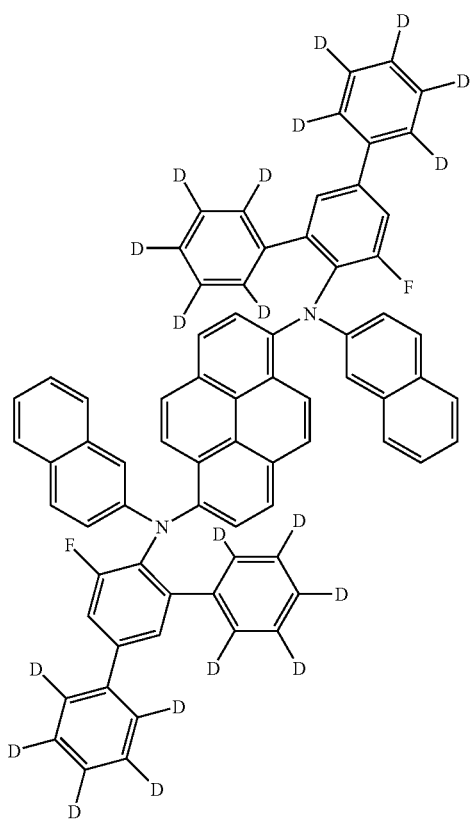

31
-continued
BD58
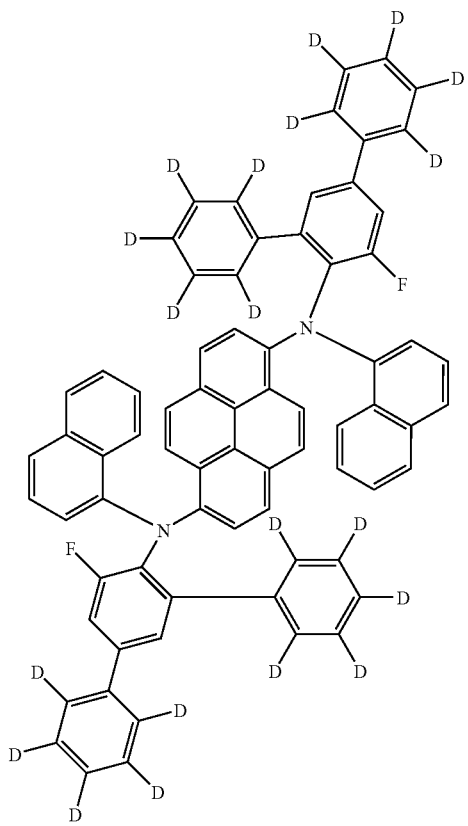
BD59
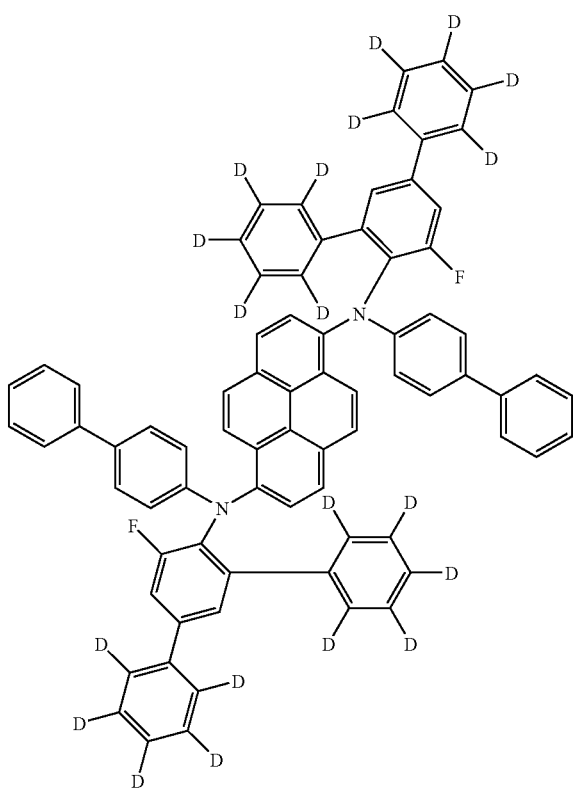
32
-continued
BD60
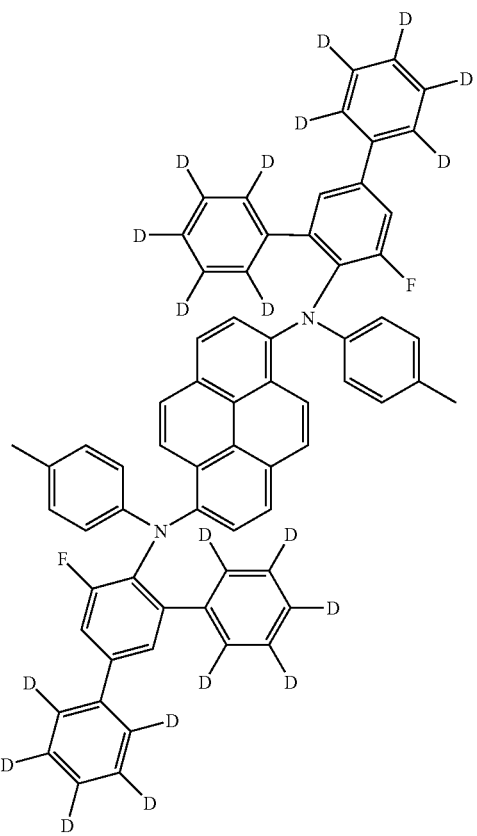
BD61
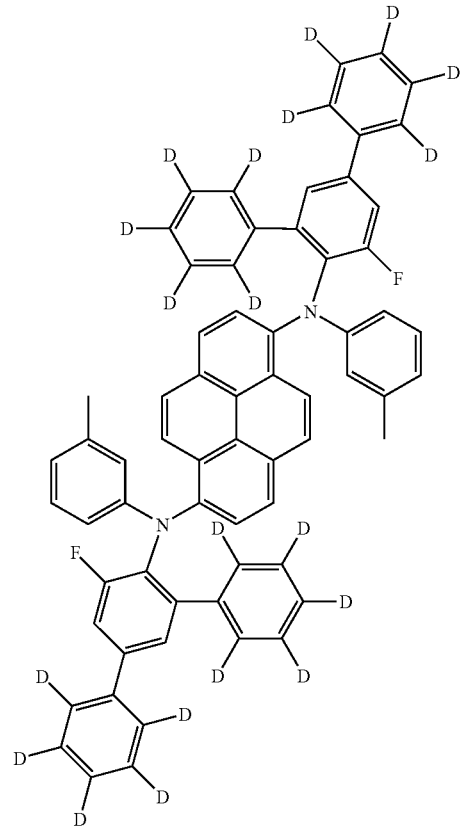

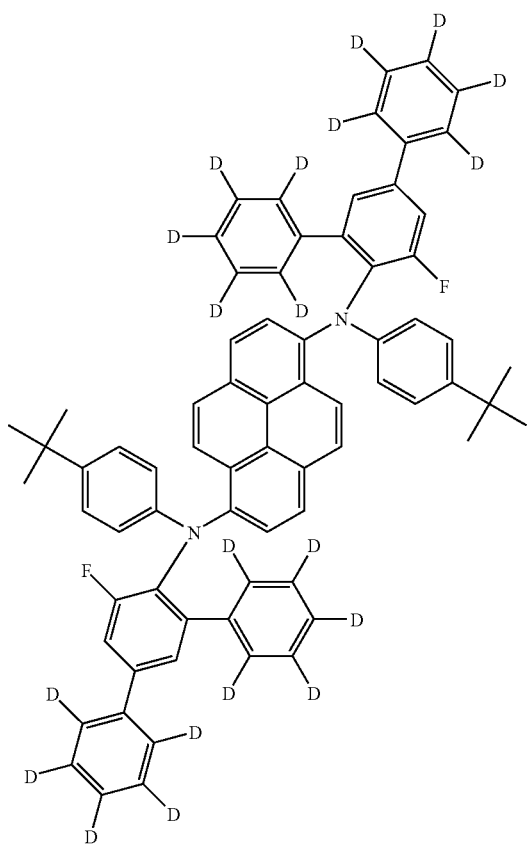
BD62
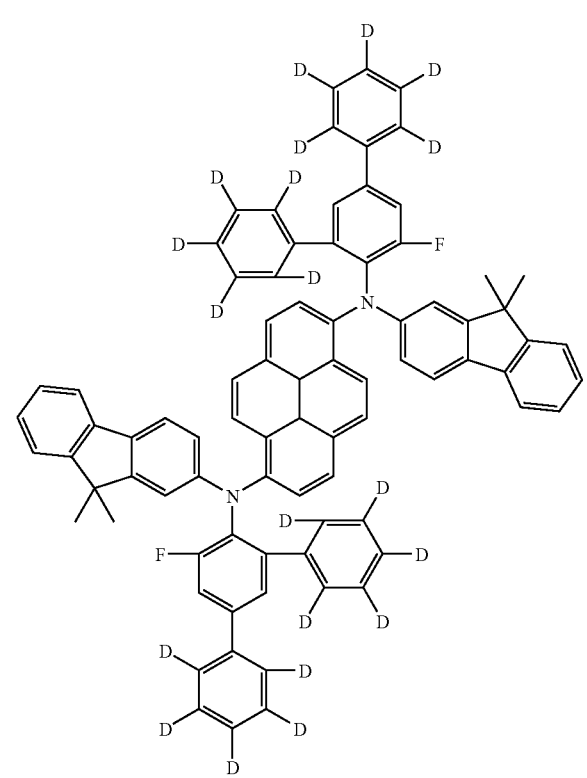
BD64
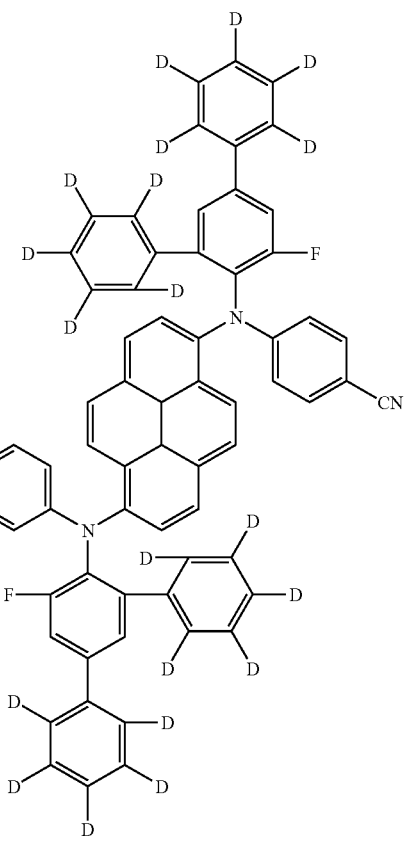
BD63
BD65

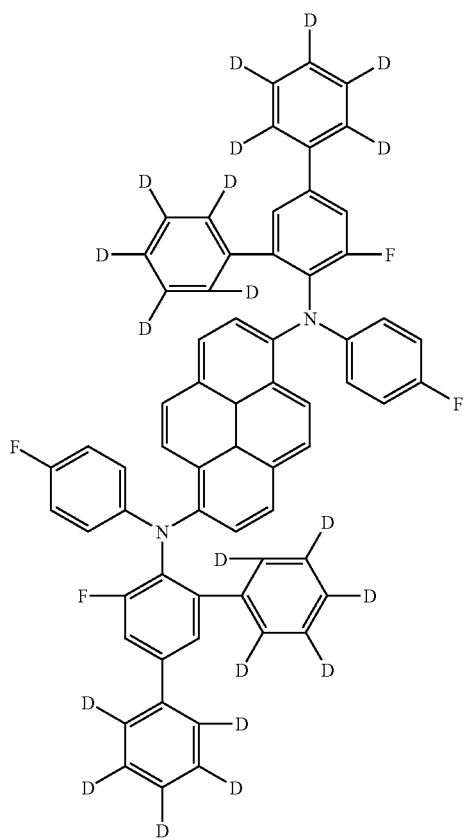
BD66
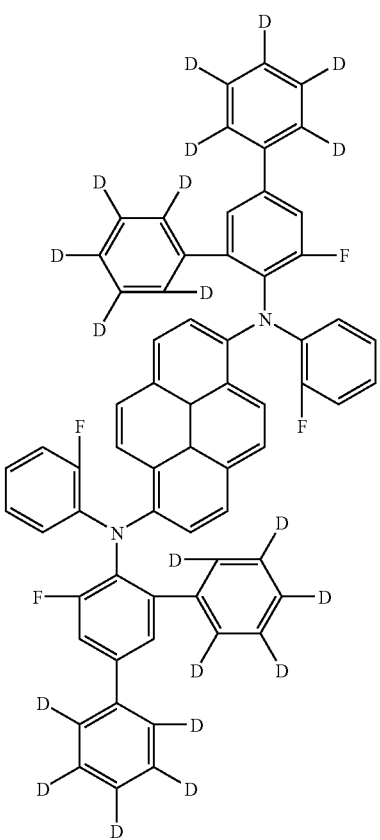
BD68
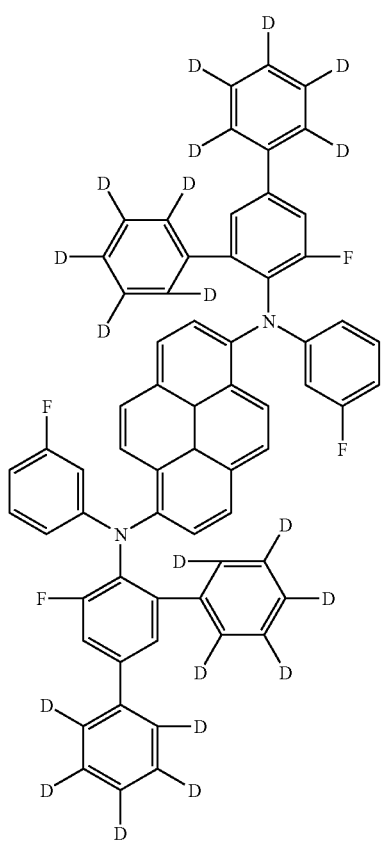
BD67
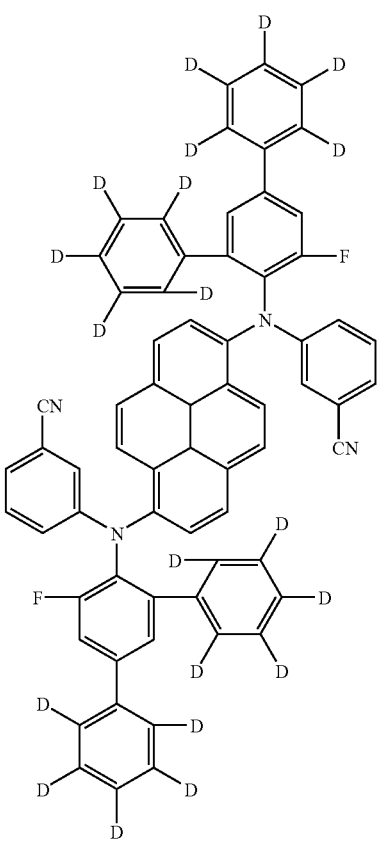
BD69

BD70
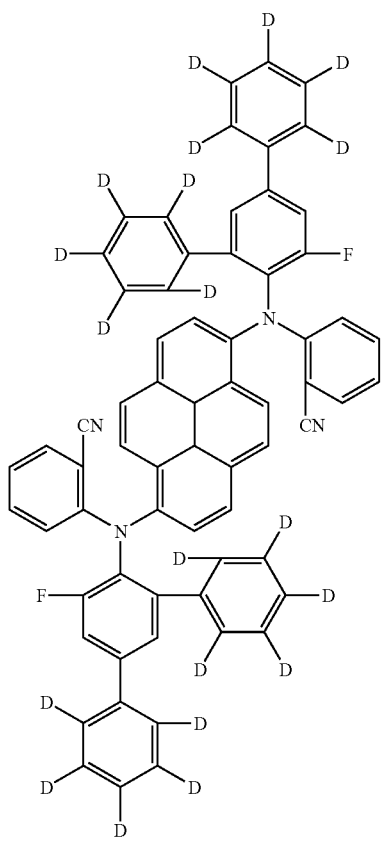
BD72
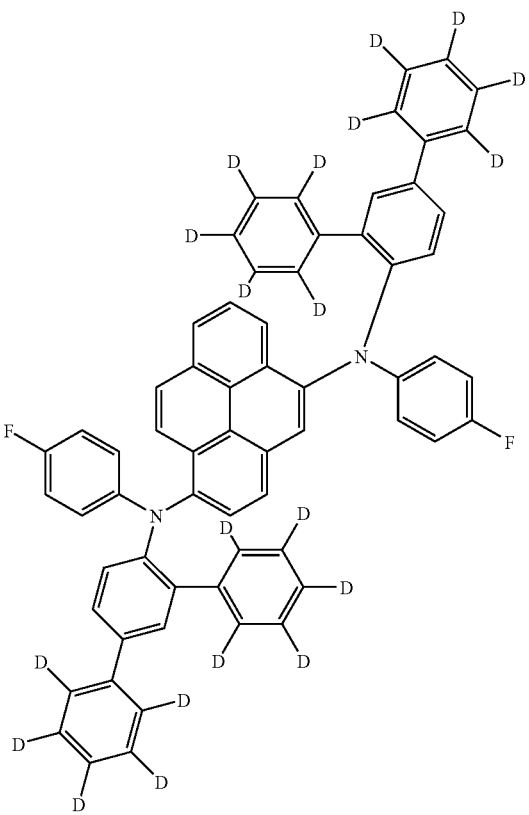
BD71
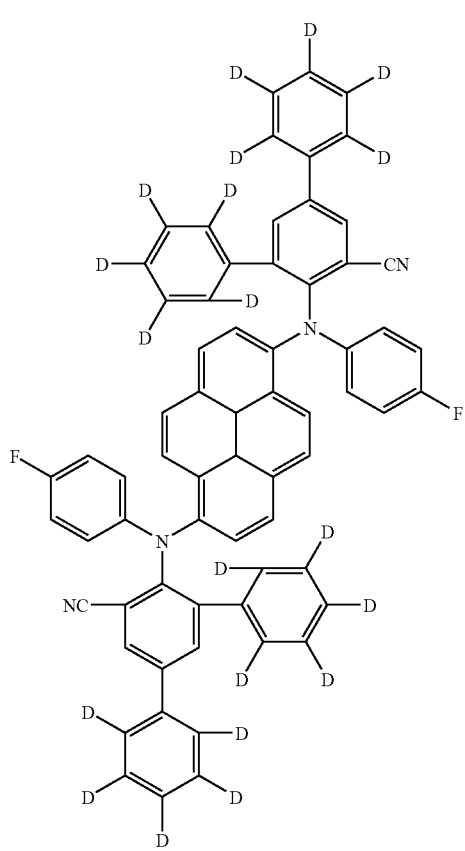
BD73
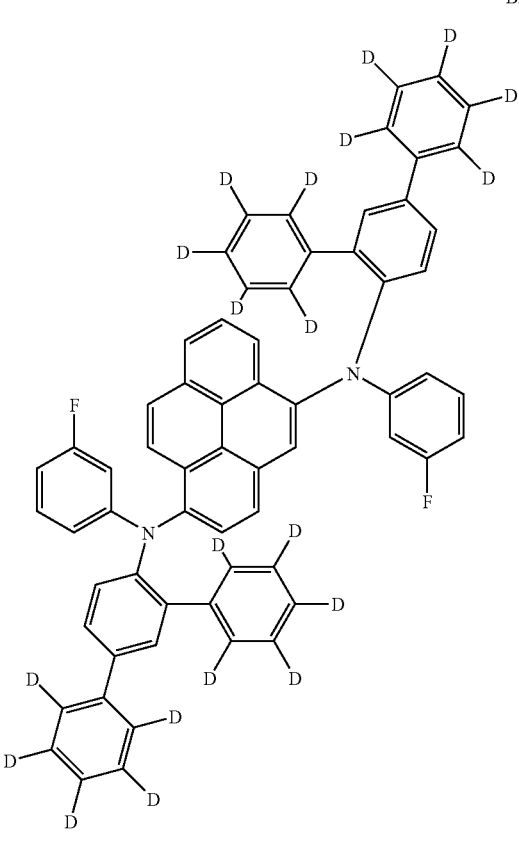

BD74
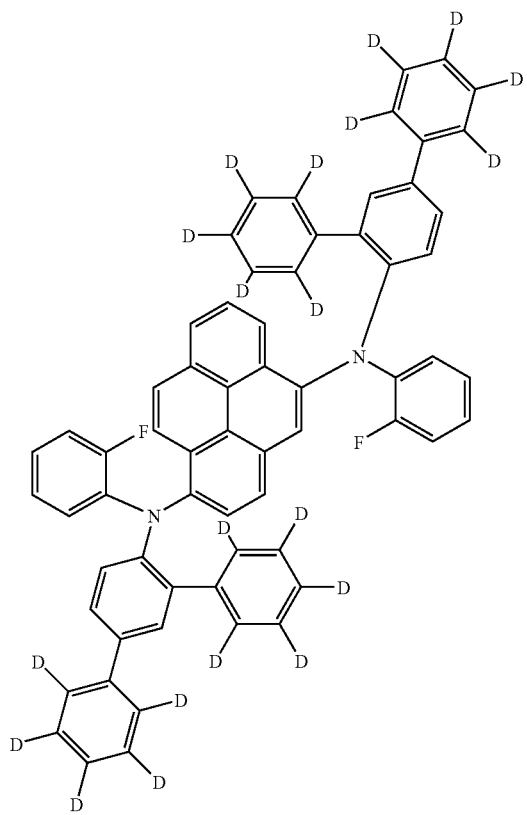
BD75
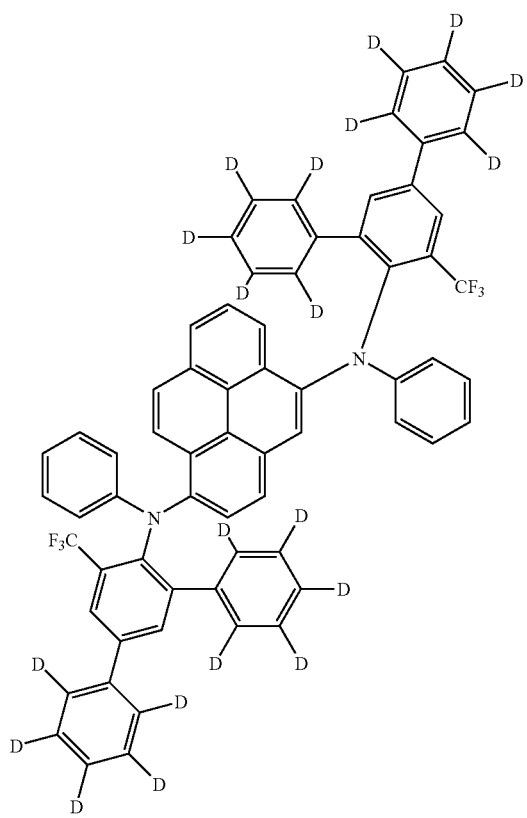
BD76
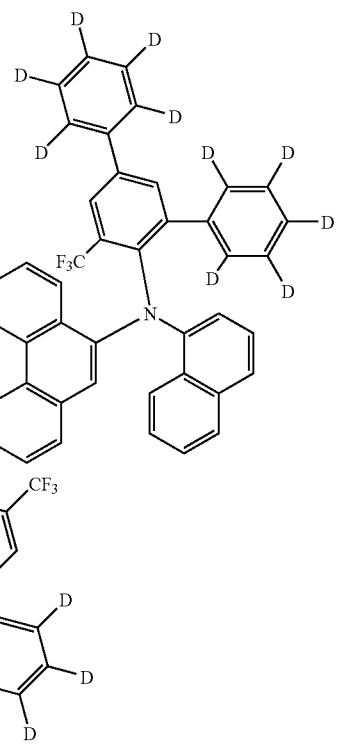
BD77
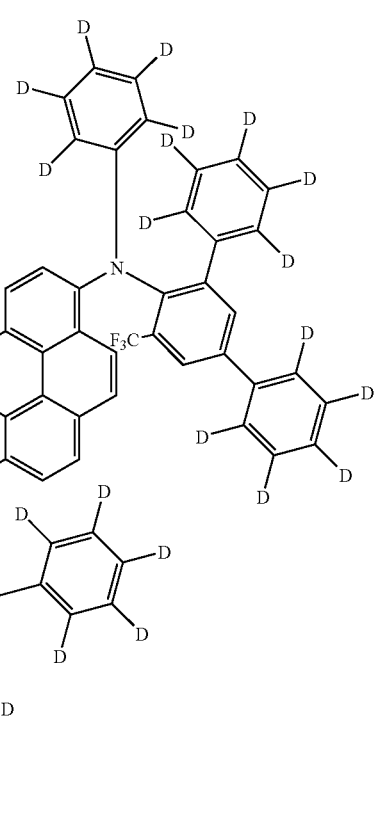

BD78
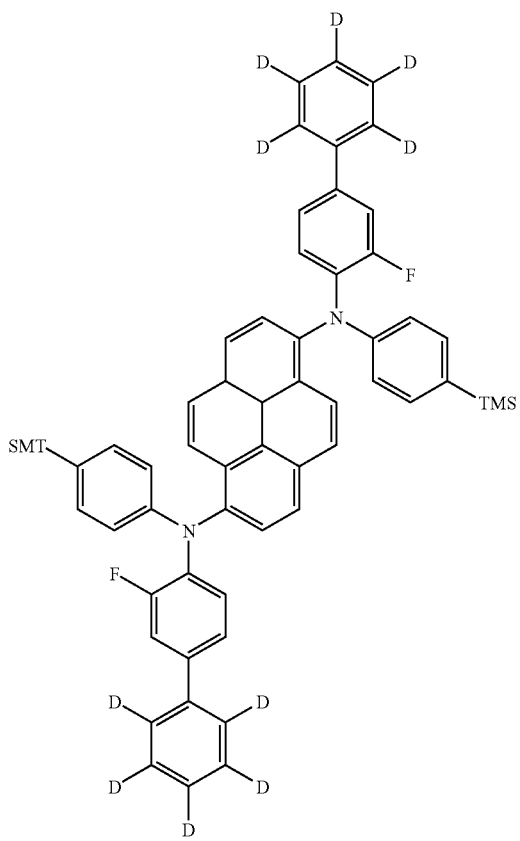
BD79
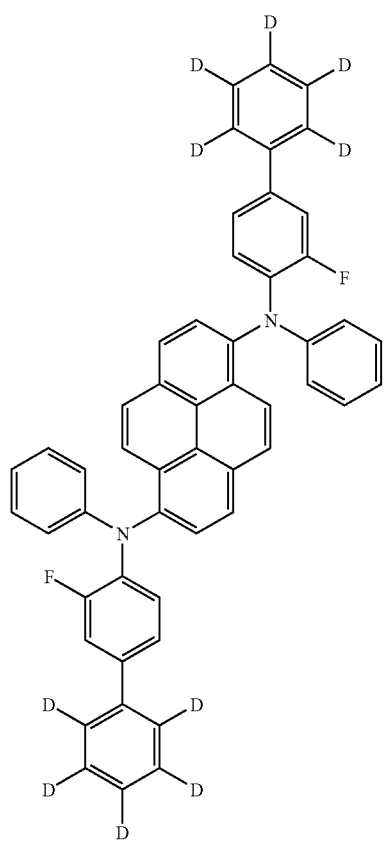
BD80
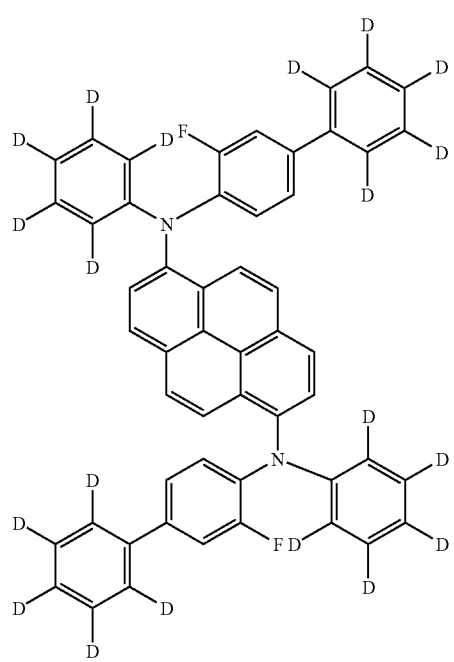
BD81
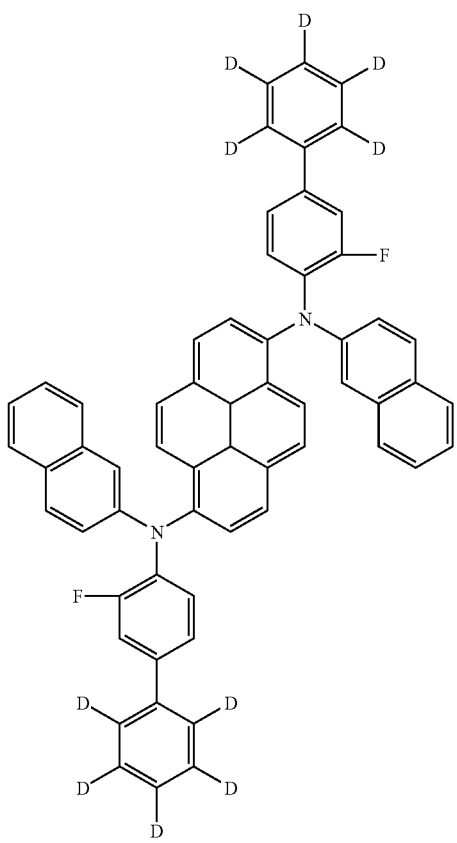

BD82
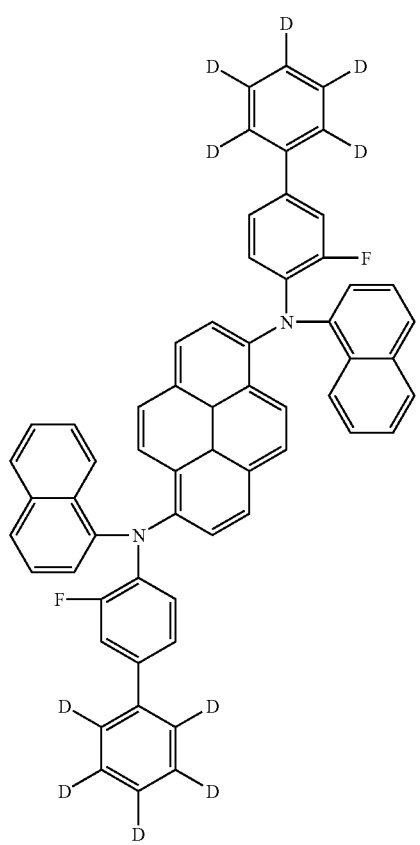
BD84
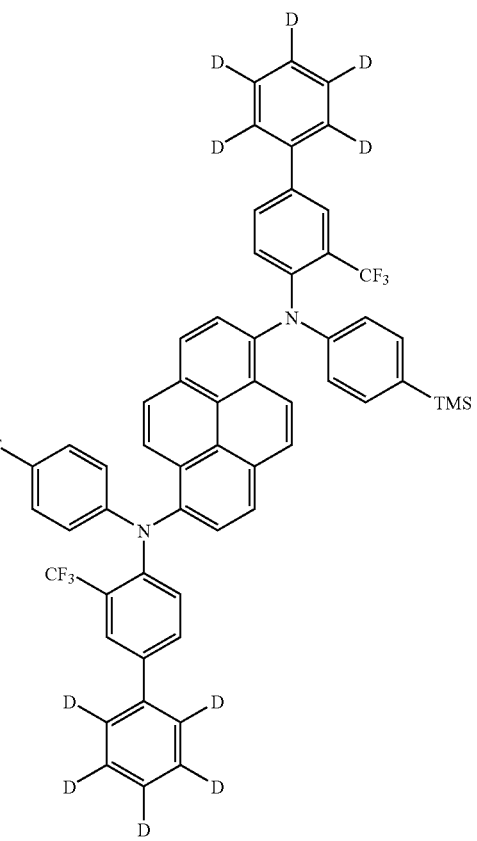
BD83
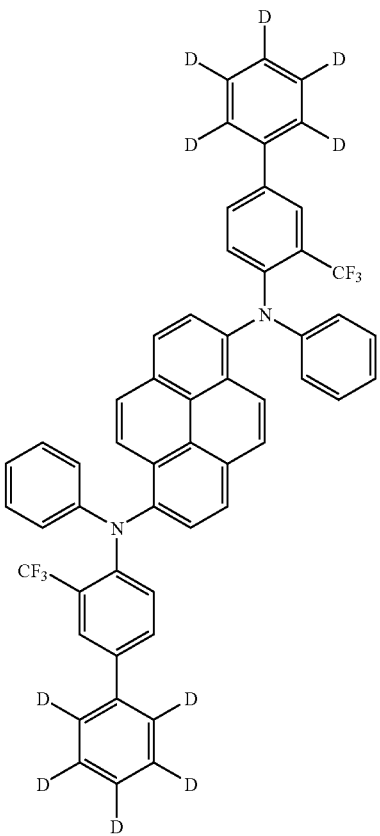
BD85

-continued

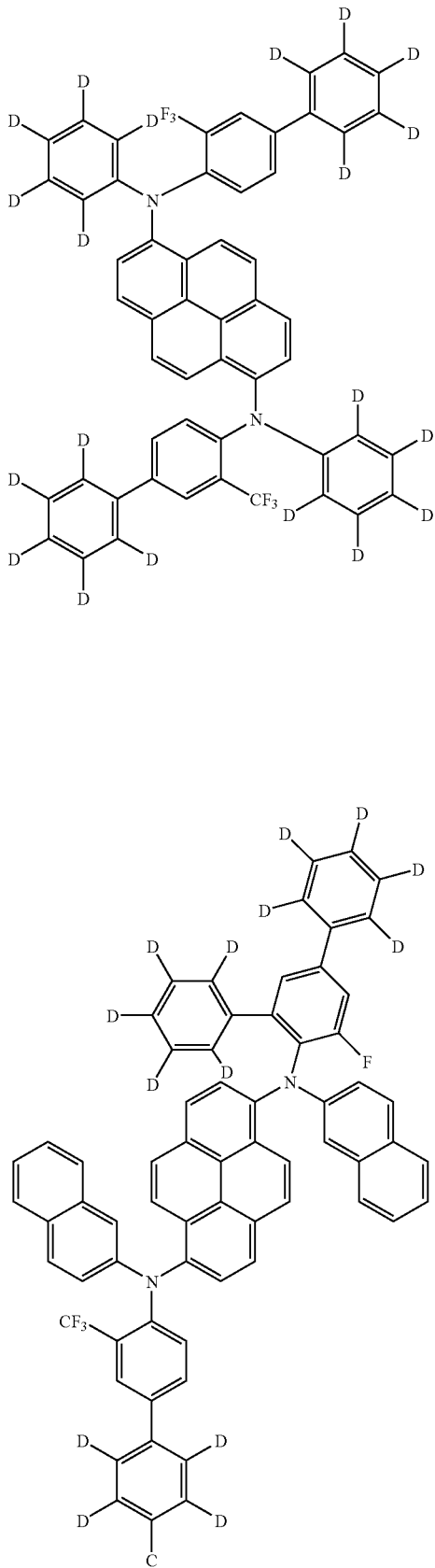

BD86

BD87

-continued

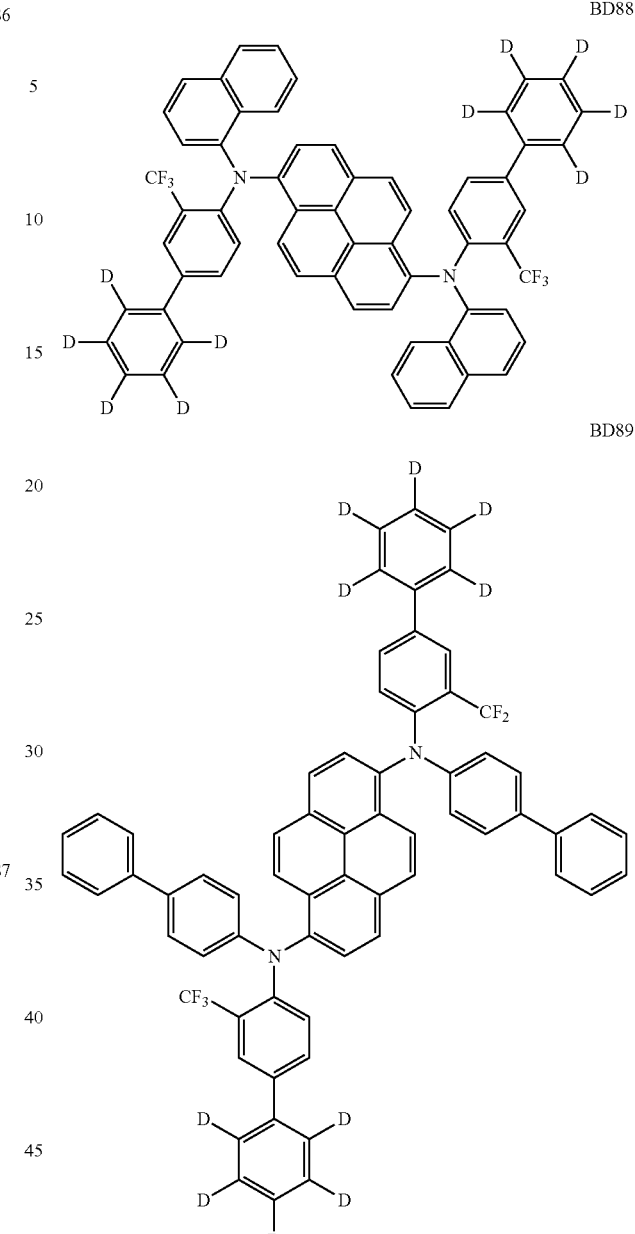

BD88

BD89

To accomplish the second object of the present invention, there is provided an organic electroluminescent device comprising an anode, a cathode and a layer interposed between the two electrodes wherein the layer contains the pyrene compound of Formula 1.

In a preferred embodiment, the layer containing the pyrene compound is a light emitting layer.

In an embodiment, the organic electroluminescent device may further comprise, between the anode and the cathode, one or more layers selected from the group consisting of a hole injecting layer (HIL), a hole transport layer (HTL), an electron blocking layer (EBL), a hole blocking layer (HBL), an electron transport layer (ETL), and an electron injecting layer (EIL).

In an embodiment, the light emitting layer may further contain one or more compounds selected from the following compounds BH1 to BH39.

BH01
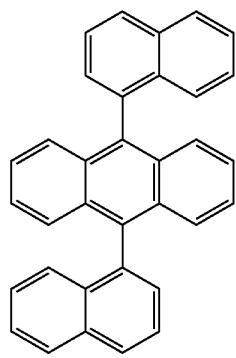
BH02
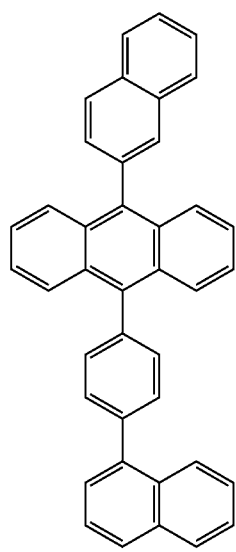
BH03
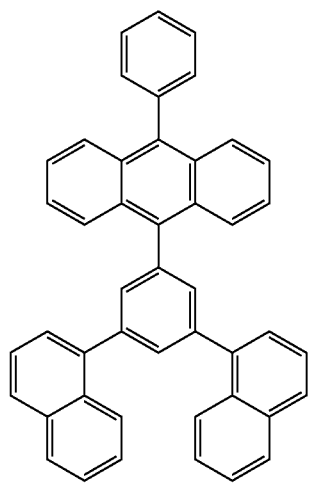
BH04
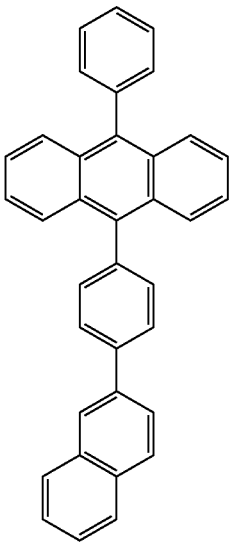
BH05
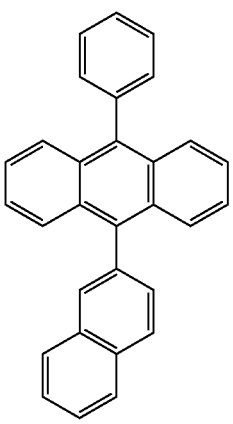
BH06
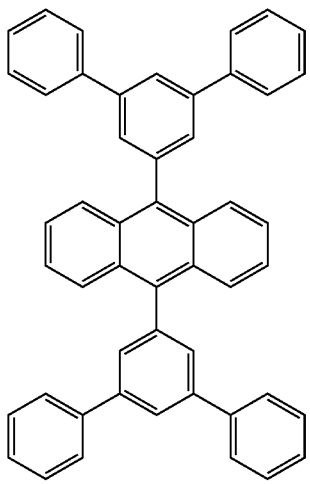

BH07
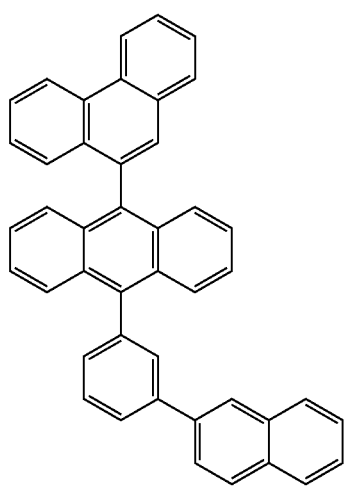
BH08
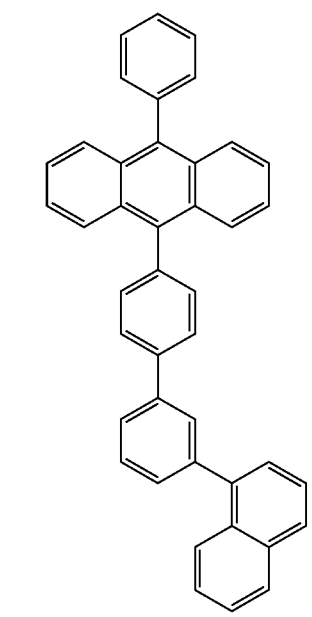
BH09
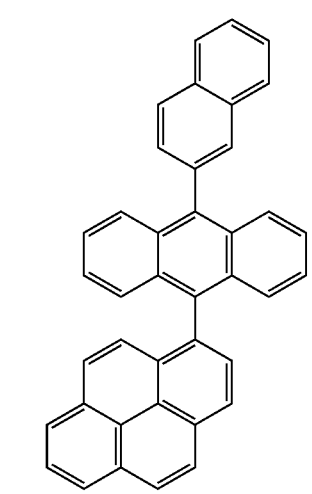
BH10
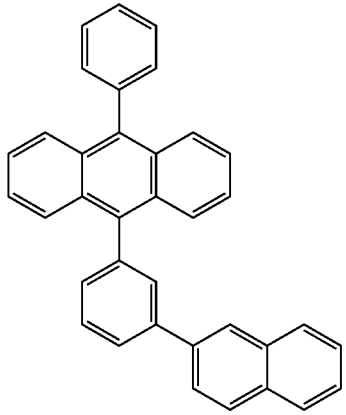
BH11
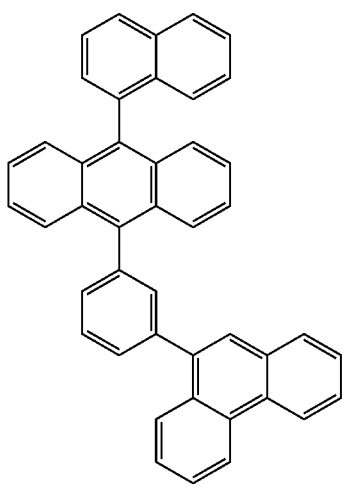
BH12
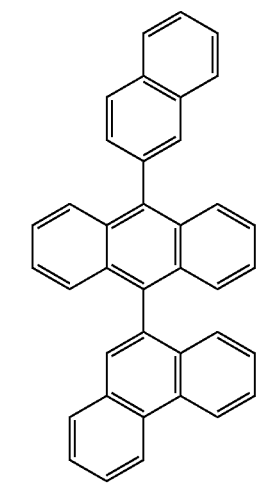

BH13
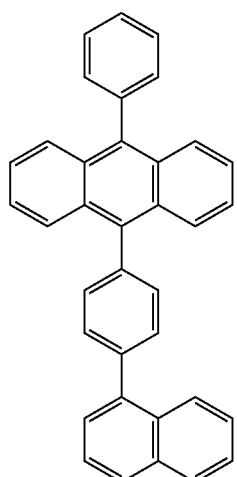
BH14
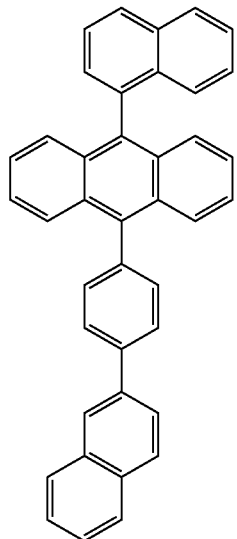
BH15
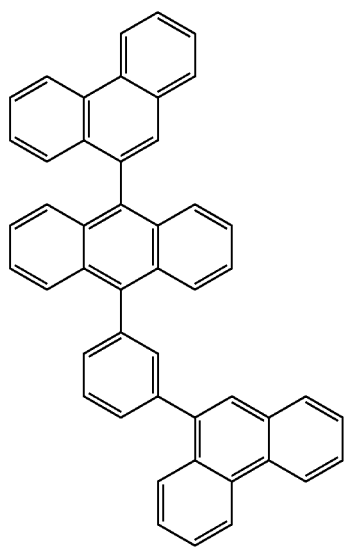
BH16
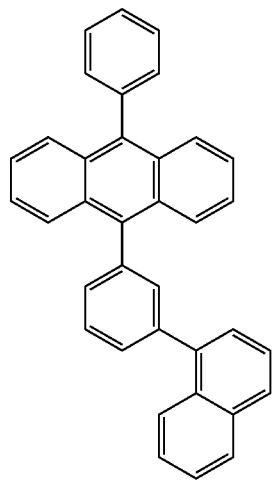
BH17
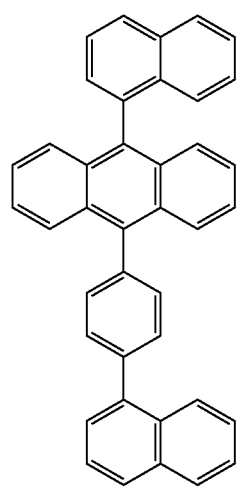
BH18
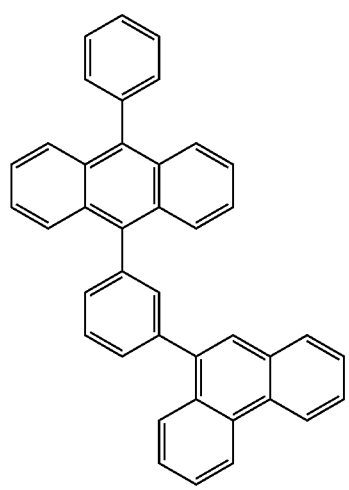

BH19
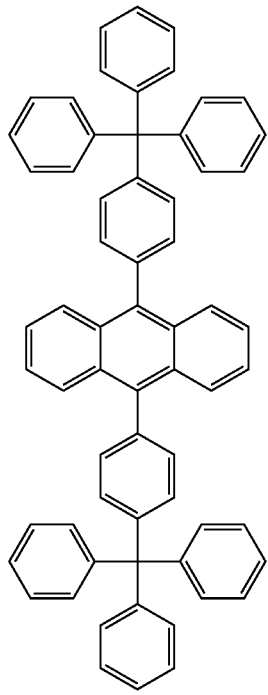
BH20
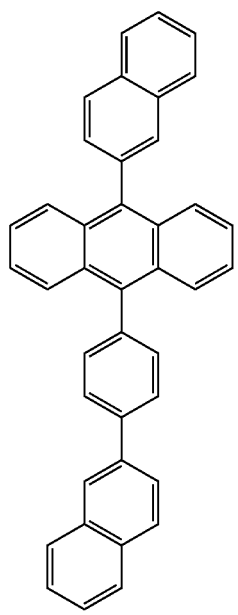
BH21
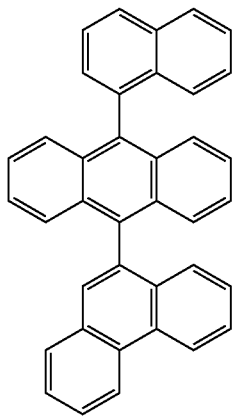
BH22
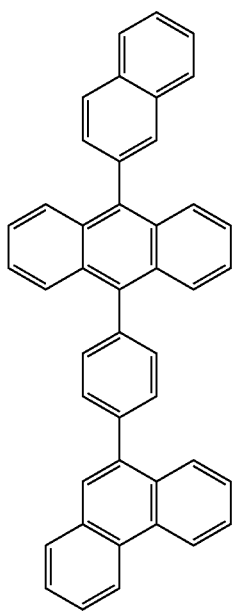
BH23
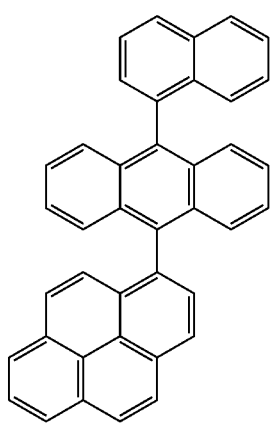

BH24
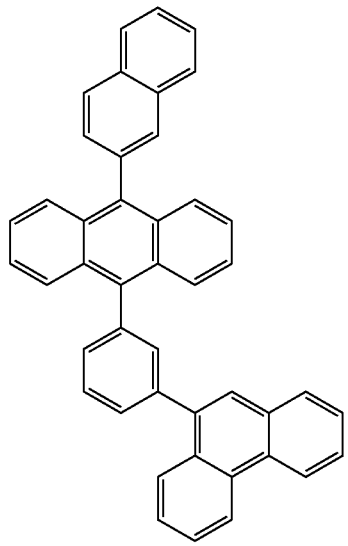
BH25
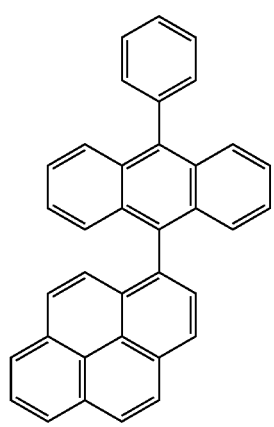
BH26
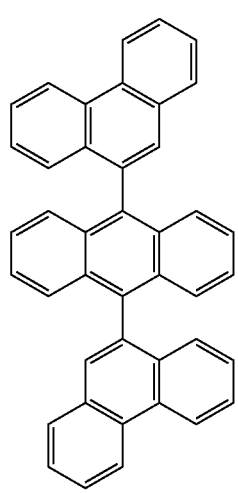
BH27
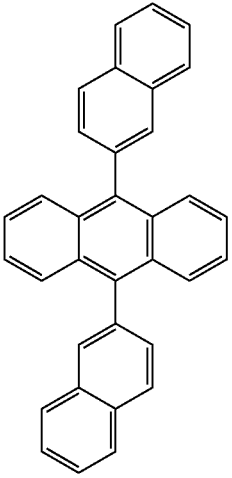
BH28
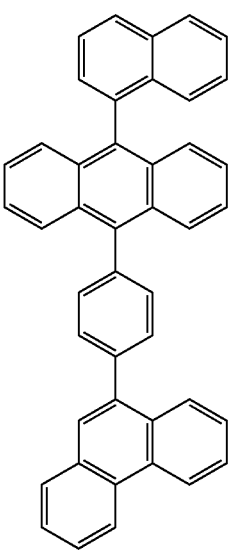
BH29
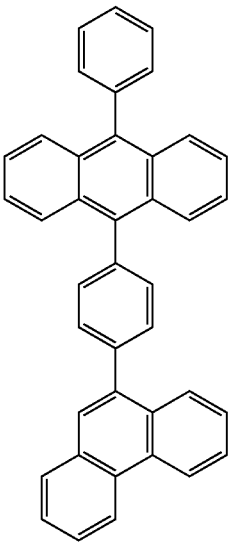

BH30
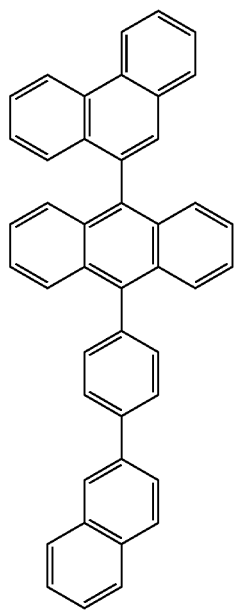
BH31
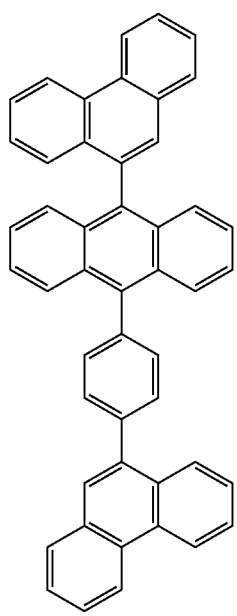
BH32
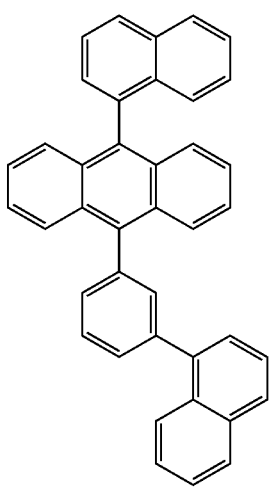
BH33
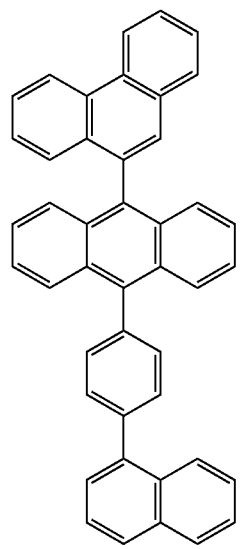
BH34
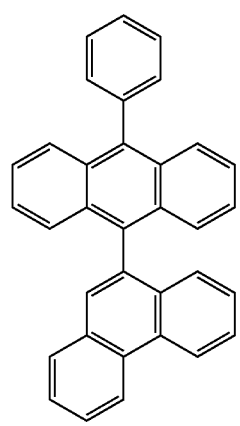

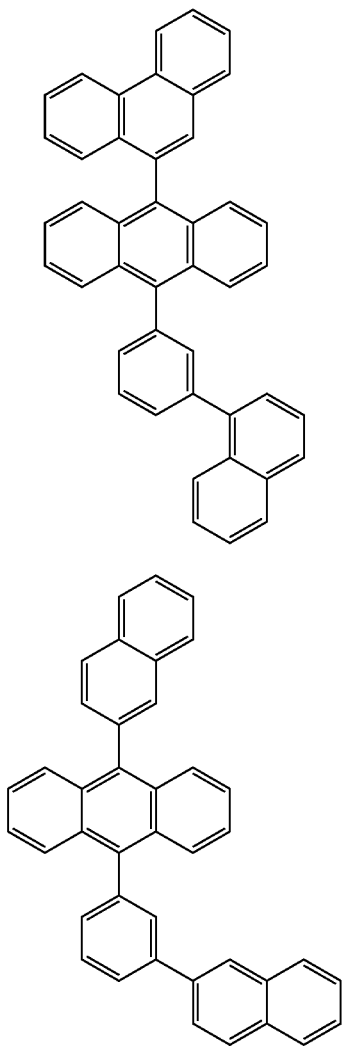

BH35

BH36

BH37

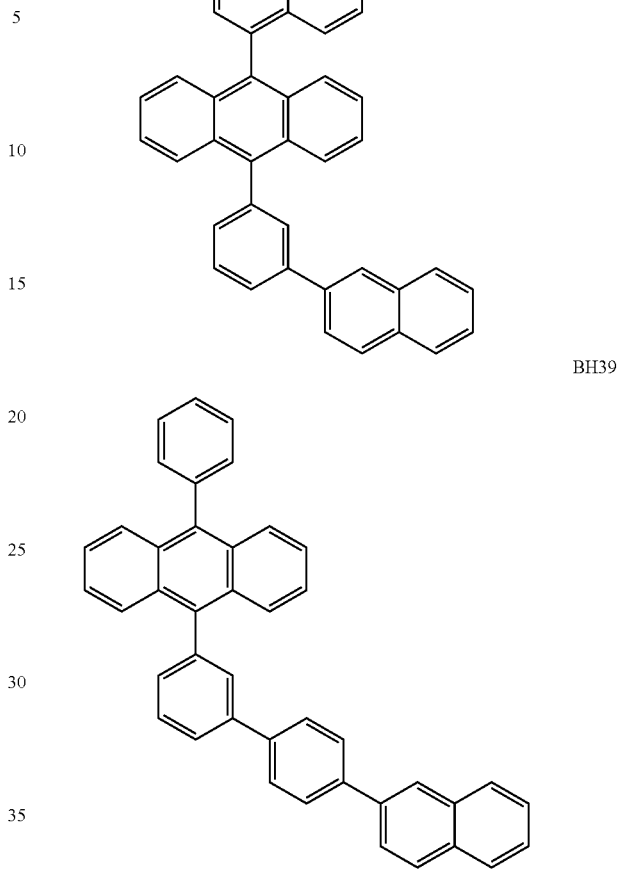

BH38

BH39

In an embodiment, at least one layer of the hole injecting layer, the hole transport layer, the electron blocking layer, the light emitting layer, the hole blocking layer, the electron transport layer and the electron injecting layer is formed by solution processing.

In an embodiment, the light emitting layer may further contain at least one compound represented by Formula 1 or at least one compound whose x and y coordinates on a 1931 CIE xy chromaticity diagram satisfy the relationship $x+y \geq 0.3$.

The organic electroluminescent device of the present invention can find application in the manufacture of displays, display devices, monochromatic lighting devices, white lighting devices, and the like.

BRIEF DESCRIPTION OF THE DRAWINGS

These and/or other aspects and advantages of the invention will become apparent and more readily appreciated from the following description of the embodiments, taken in conjunction with the accompanying drawings of which.

DETAILED DESCRIPTION OF THE INVENTION

Figure 1:
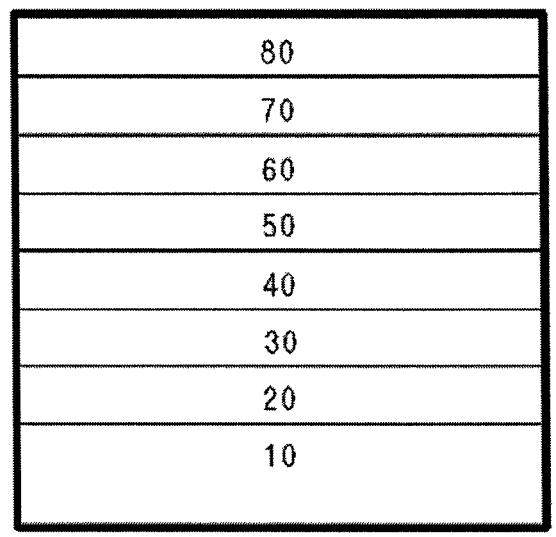
FIG. 1 is a schematic view of an organic electroluminescent device according to an embodiment of the present invention.
Figure 2:
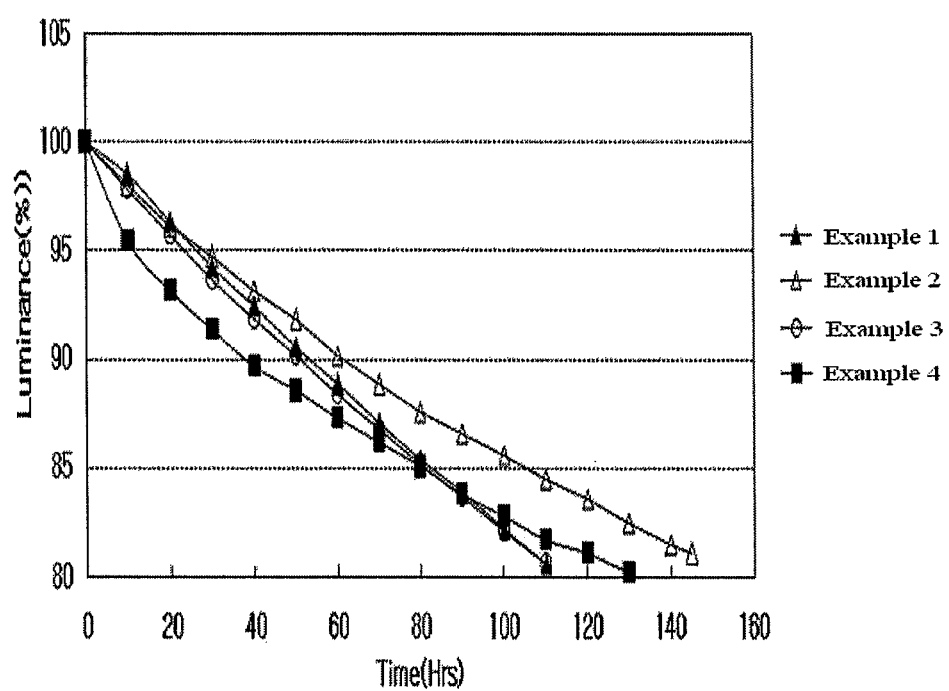
FIG. 2 is a graph showing changes in the luminance of organic electroluminescent devices fabricated in Examples 1 to 4 as a function of time.
Figure 3:
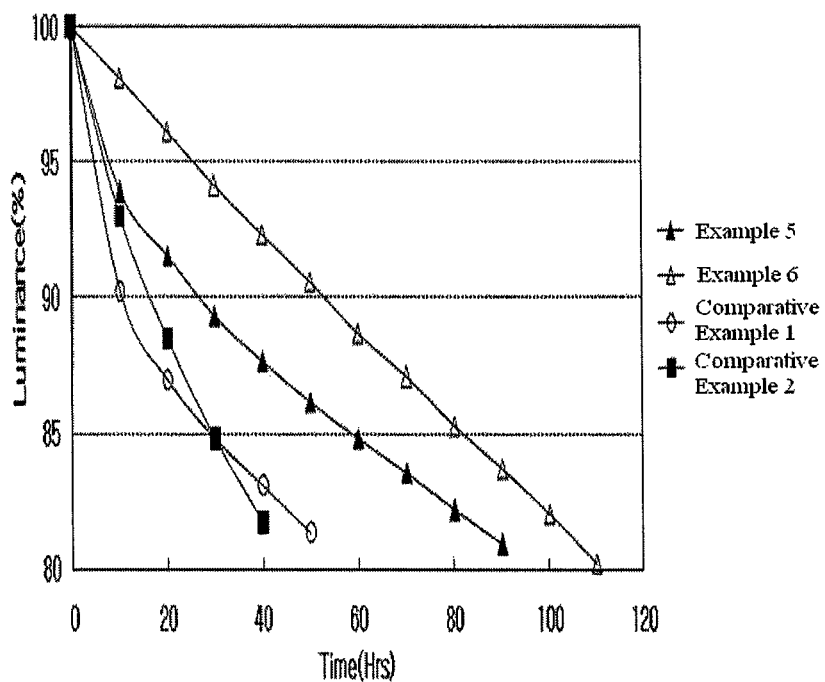
FIG. 3 is a graph showing changes in the luminance of organic electroluminescent devices fabricated in Examples 5 and 6 and Comparative Examples 1 and 2 as a function of time.
Figure 4:
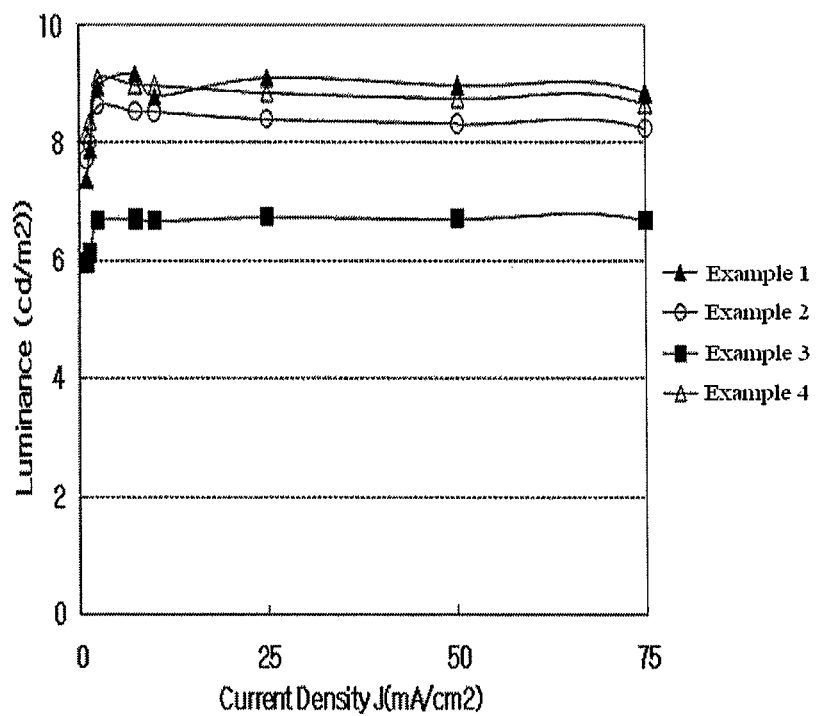
FIG. 4 is a graph showing changes in the relative luminance (T80) of organic electroluminescent devices fabricated in Examples 1 to 4 as a function of current density.
Figure 5:
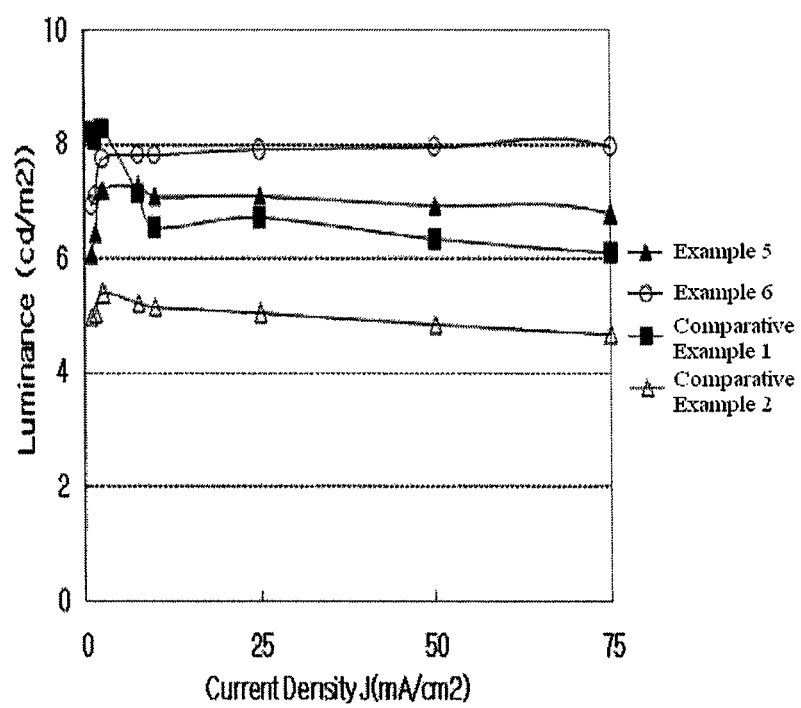
FIG. 5 is a graph showing changes in the relative luminance (T80) of organic electroluminescent devices fabricated in Examples 5 and 6 and Comparative Examples 1 and 2 as a function of current density.

The pyrene compound of Formula 1 according to the present invention emits blue light, and has a structure in which an amine derivative of pyrene is substituted with at least one deuterium atom and at least one halogen atom to achieve improved color purity and life characteristics.

The organic electroluminescent device of the present invention has a structure in which an anode, a cathode and a layer interposed between the two electrodes and containing the pyrene compound of Formula 1. The organic electroluminescent device of the present invention can be used in a variety of applications, such as displays and lighting systems, due to the high color purity of the blue light emitting compound.

Specifically, the pyrene compound of the present invention is represented by Formula 1:

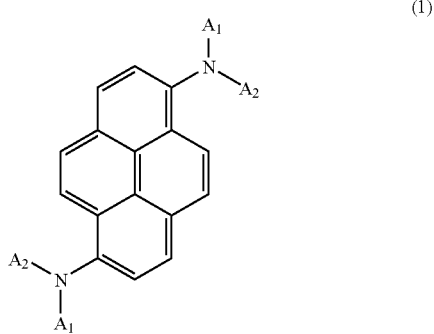

(1)

wherein $A_1$ and $A_2$ are each independently a $C_6$-$C_{24}$ aryl or $C_2$-$C_{24}$ heteroaryl group which is unsubstituted or substituted with at least one substituent selected from the group consisting of substituted $C_1$-$C_{24}$ alkyl groups, unsubstituted $C_1$-$C_{24}$ alkyl groups, substituted $C_3$-$C_{24}$ cycloalkyl groups, unsubstituted $C_3$-$C_{24}$ cycloalkyl groups, substituted $C_1$-$C_{24}$ alkoxy groups, unsubstituted $C_1$-$C_{24}$ alkoxy groups, cyano groups, halogen groups, substituted $C_6$-$C_{24}$ aryl groups, unsubstituted $C_6$-$C_{24}$ aryl groups, substituted $C_6$-$C_{24}$ aryloxy groups, unsubstituted $C_6$-$C_{24}$ aryloxy groups, substituted $C_2$-$C_{24}$ heteroaryl groups, unsubstituted $C_2$-$C_{24}$ heteroaryl groups, substituted $C_6$-$C_{40}$ arylamino groups, unsubstituted $C_6$-$C_{40}$ arylamino groups, substituted $C_2$-$C_{40}$ alkylamino groups, unsubstituted $C_2$-$C_{40}$ alkylamino groups, germanium, boron, substituted $C_1$-$C_{24}$ alkylsilyl groups, unsubstituted $C_1$-$C_{24}$ alkylsilyl groups, substituted $C_1$-$C_{24}$ arylsilyl groups, unsubstituted $C_1$-$C_{24}$ arylsilyl groups, and deuterium, with the proviso that the pyrene compound contains at least one deuterium atom and at least one halogen atom.

In a preferred embodiment, $A_1$ or $A_2$ is substituted or unsubstituted phenyl, substituted or unsubstituted naphthyl, substituted or unsubstituted pyridinyl, phenanthryl, substituted or unsubstituted biphenyl or substituted or unsubstituted terphenyl.

In a preferred embodiment, the substitutent of $A_1$ or $A_2$ contains at least one halogen atom. In a more preferred embodiment, the halogen atom is a fluorine atom (F).

In an embodiment, the pyrene compound may be selected from the group consisting of, but not limited to, the compounds represented by Formulas BD1 to BD89.

Specific examples of alkyl groups suitable for use as substituents in the pyrene compound of the present invention include methyl, ethyl, propyl, isobutyl, sec-butyl, tert-butyl, pentyl, iso-amyl, hexyl, heptyl, octyl, stearyl, trichloromethyl and trifluoromethyl. At least one hydrogen atom of each alkyl group may be substituted with a deuterium atom, a halogen atom, a hydroxyl group, a nitro group, a cyano group, a trifluoromethyl group, a silyl group (herein, referred to as an "alkylsilyl group"), a substituted or unsubstituted amino group (—NH$_2$, —NH(R) or —N(R')(R") wherein R' and R" are independently a $C_1$-$C_{20}$ alkyl group, the —NH(R) and —N(R')(R") are referred to as "alkylamino groups"), an amidino group, a hydrazine group, a hydrazone group, a carboxyl group, a sulfonic acid group, a phosphoric acid group, a $C_1$-$C_{20}$ alkyl group, a $C_1$-$C_{20}$ halogenated alkyl group, a $C_1$-$C_{20}$ alkenyl group, a $C_1$-$C_{20}$ alkynyl group, a $C_1$-$C_{20}$ heteroalkyl group, a $C_6$-$C_{30}$ aryl group, a $C_6$-$C_{60}$ arylalkyl group, a $C_4$-$C_{40}$ heteroaryl group, or a $C_4$-$C_{40}$ heteroarylalkyl group.

Specific examples of cycloalkyl groups suitable for use as substituents in the pyrene compound of the present invention include cyclopropyl, cyclopentyl, cyclohexyl, cycloheptyl, cyclooctyl, and adamantyl. These cycloalkyl groups may be substituted with the same substitutents as in the alkyl groups.

Specific examples of alkoxy groups suitable for use as substituents in the pyrene compound of the present invention include methoxy, ethoxy, propoxy, isobutyloxy, sec-butyloxy, pentyloxy, iso-amyloxy and hexyloxy. These alkoxy groups may be substituted with the same substitutents as in the alkyl groups.

Specific examples of halogen groups suitable for use as substituents in the pyrene compound of the present invention include fluorine (F), chlorine (Cl) and bromine (Br) groups.

Specific examples of aryl groups suitable for use as substituents in the pyrene compound of the present invention include aromatic groups, such as phenyl, 2-methylphenyl, 3-methylphenyl, 4-methylphenyl, 4-ethylphenyl, o-biphenyl, m-biphenyl, p-biphenyl, 4-methylbiphenyl, 4-ethylbiphenyl, o-terphenyl, m-terphenyl, p-terphenyl, 1-naphthyl, 2-naphthyl, 1-methylnaphthyl, 2-methylnaphthyl, anthryl, phenanthryl, pyrenyl, fluorenyl and tetrahydronaphthyl. These aryl groups may be substituted with the same substitutents as in the alkyl groups.

Specific examples of heteroaryl groups suitable for use as substituents in the pyrene compound of the present invention include pyridinyl, pyrimidinyl, triazinyl, indolinyl, quinolinyl, pyrrolidinyl, piperidinyl, morpholidinyl, piperadinyl, carbazolyl, oxazolyl, oxadiazolyl, benzoxazolyl, thiazolyl, thiadiazolyl, benzothiazolyl, triazolyl, imidazolyl and benzimidazolyl. These heteroaryl groups may be substituted with the same substitutents as in the alkyl groups.

The organic electroluminescent device of the present invention comprises an anode, a cathode and a layer interposed between the two electrodes in which the layer contains the pyrene compound of Formula 1. In a preferred embodiment, the layer containing the pyrene compound of Formula 1 is a light emitting layer. In an embodiment, the organic electroluminescent device may further comprise, between the anode and the cathode, one or more layers selected from the group consisting of a hole injecting layer, a hole transport layer, an electron blocking layer, a hole blocking layer, an electron transport layer and an electron injecting layer.

In an embodiment, the light emitting layer may further contain one or more compounds selected from the compounds BH1 to BH39.

In an embodiment, at least one layer of the hole injecting layer, the hole transport layer, the electron blocking layer, the light emitting layer, the hole blocking layer, the electron transport layer and the electron injecting layer is formed by solution processing.

In an embodiment, the light emitting layer may further contain at least one compound represented by Formula 1 or at least one compound whose x and y coordinates on a 1931 CIE xy chromaticity diagram satisfy the relationship $x+y \geqq 0.3$.

Specifically, a hole transport layer may be further disposed between the anode and the organic light emitting layer, and an electron transport layer may be further disposed between the cathode and the organic light emitting layer. The hole transport layer serves to facilitate the injection of holes from the anode. An electron-donating compound having a low ionization potential is used as a material for the hole transport layer. A diamine, triamine or tetraamine derivative whose basic skeleton is triphenylamine is mainly used.

Any suitable hole transport material known in the art may be used without particular limitation to form the hole transport layer, and examples thereof N,N'-bis(3-methylphenyl)-N,N'-diphenyl-[1,1'-biphenyl]-4,4'-diamine (TPD) and N,N'-di(naphthalen-1-yl)-N,N'-diphenylbenzidine (α-NPD).

The organic electroluminescent device of the present invention may further comprise a hole injecting layer disposed under the hole transport layer. The hole injecting layer may be formed of any suitable material commonly used in the art, for example, CuPc or a starburst-type amine (e.g., TCTA or m-MTDATA).

The electron transport layer serves to sufficiently transport electrons from the cathode to the organic light-emitting layer. Another role of the electron transport layer is to inhibit the migration of unbound holes in the organic light-emitting layer, thereby increasing the opportunity for the unbound holes to recombine with the electrons in the light-emitting layer. It is to be understood that the electron transport layer can be formed of any suitable material commonly used in the art, for example, an oxadiazole derivative, such as PBD, BMD, BND or $Alq_3$.

The organic electroluminescent device of the present invention may further comprise an electron injecting layer disposed on the electron transport layer to facilitate the injection of electrons from the cathode. The formation of the electron injecting layer contributes to an improvement in the power efficiency of the device. Any suitable electron injecting material known in the art may be used without particular limitation to form the electron injecting layer, and examples thereof include LiF, NaCl, CsF, $Li_2O$ and BaO.

The organic electroluminescent device of the present invention can find application in the manufacture of displays, display devices, monochromatic lighting devices, white lighting devices, and the like.

FIG. 1 is a cross-sectional view illustrating an exemplary structure of the organic electroluminescent device according to the present invention. Referring to FIG. 1, the organic electroluminescent device of the present invention comprises an anode 20, a hole transport layer 40, an organic light-emitting layer 50, an electron transport layer 60, and a cathode 80. If necessary, the organic electroluminescent device may further comprise a hole injecting layer 30 and an electron injecting layer 70. In addition to the hole and electron injecting layers 30 and 70, the organic electroluminescent device may further comprise one or two intermediate layers. Also, the organic electroluminescent device may further comprise a hole blocking layer or an electron blocking layer.

A method for fabricating the organic electroluminescent device of the present invention will be explained below with reference to FIG. 1. First, an anode material is coated on a substrate 10 to form an anode 20. The substrate 10 may be a substrate used in common organic electroluminescent (EL) devices. An organic substrate or a transparent plastic substrate is preferred in terms of transparency, surface smoothness, ease of handling and waterproofness. As the anode material, there may be used a highly transparent and electrically conductive material, for example, indium tin oxide (ITO), indium zinc oxide (IZO), tin oxide ($SnO_2$) or zinc oxide (ZnO).

A hole injecting material is applied to the anode 20 by vacuum thermal evaporation or spin coating to form a hole injecting layer 30. Next, a hole transport material is applied to the hole injecting layer 30 by vacuum thermal evaporation or spin coating to form a hole transport layer 40. Subsequently, an organic light-emitting layer 50 is formed on the hole transport layer 40, and optionally a hole blocking layer (not shown) may be formed on the organic light-emitting layer 50 by vacuum deposition or spin coating. The hole blocking layer is formed of a material having a very low HOMO level to avoid the problems (i.e. short lifetime and low efficiency of the device) encountered when holes enter the cathode through the organic light-emitting layer. The hole blocking material is not particularly restricted so long as it has a higher ionization potential than the light-emitting compound while possessing the ability to transport electrons. Representative examples of the hole blocking material are BAlq, BCP and TPBI.

An electron transport layer 60 is formed on the hole blocking layer by vacuum deposition or spin coating, and an electron injecting layer 70 is formed thereon. A cathode metal is deposited to the electron injecting layer 70 by vacuum thermal evaporation to form a cathode 80, completing the fabrication of the organic EL device. As the cathode metal, there may be used, for example, lithium (Li), magnesium (Mg), aluminum (Al), aluminum-lithium (Al—Li), calcium (Ca), magnesium-indium (Mg—In) or magnesium-silver (Mg—Ag). When it is intended to fabricate a top emission type organic EL device, a light-transmissive cathode made of ITO or IZO can be used.

Hereinafter, the present invention will be explained in more detail with reference to the following examples. However, these examples are given for illustrative purposes only and are not intended to limit the present invention.

EXAMPLES

Preparative Example 1

Synthesis of Compound BD51

Preparative Example 1-(1)

Synthesis of 2,4-bis(phenyl-$d_5$)-6-fluoroaniline 30 g (111.56 mmol) of 2,4-dibromo-6-fluoroaniline, 31.2 g (245.44 mmol) of phenylboronic acid-$d_5$, 61.9 g (446.27 mmol) of potassium carbonate ($K_2CO_3$), 2.6 g (2.20 mmol) of tetrakis(triphenylphosphine)palladium (Pd(PPh$_3$)$_4$), 120 mL of water, 300 mL of toluene and 300 mL of tetrahydrofuran were refluxed in a 1 L round bottom flask for 24 hr. After completion of the reaction, the organic layer was separated from the aqueous layer and was concentrated under reduced pressure. The concentrate was purified by column chromatography using hexane/dichloromethane as the eluent and dried to give 24.2 g (yield 79.4%) of the title compound as a white solid.

Preparative Example 1-(2)

Synthesis of N-[2,4-bis(phenyl-d$_5$)-6-fluorobenzo]-N'-(biphenyl-4-yl)amine 20.0 g of (73.16 mmol) of the compound 2,4-bis(phenyl-d$_5$)-6-fluoroaniline prepared in Preparative Example 1-(1), 17.90 g (76.82 mmol) of 4-bromobiphenyl, 0.33 g (1.46 mmol) of palladium acetate (Pd(OAc)$_2$), 14.06 g (146.32 mmol) of sodium tert-butoxide, 0.91 g (1.46 mmol) of 2,2'-bisdiphenylphosphino-1,1'-binaphthyl and 180 mL of toluene were refluxed in a 250 mL round bottom flask for 24 hr. After completion of the reaction, the hot reaction mixture was filtered, distilled under reduced pressure to remove the toluene, and subjected to column chromatography. The eluate was dissolved in dichloromethane. Hexane was added to the dichloromethane solution to precipitate a crystal. The crystal was collected by filtration and dried to give 23.1 g (yield 70.7%) of the title compound as a white solid.

Preparative Example 1-(3)

Synthesis of Compound BD51

23.7 g (53.33 mmol) of the compound N-[2,4-bis(phenyl-d$_5$)-6-fluorobenzo]-N'-(biphenyl-4-yl)amine prepared in Preparative Example 1-(2), 8 g (22.22 mmol) of dibromopyrene, 0.10 g (0.44 mmol) of palladium acetate (Pd(OAc)$_2$), 8.54 g (88.89 mmol) of sodium tert-butoxide, 0.18 g (0.89 mmol) of tri-tert-butylphosphine and 300 mL of toluene were refluxed in a 500 mL round bottom flask for 24 hr. After completion of the reaction, the reaction mixture was cooled to room temperature to precipitate a crystal. The crystal was collected by filtration and dissolved in toluene. Ethanol was added to the toluene solution to precipitate a crystal. The crystal was again collected by filtration and dried to give 9.5 g (yield 40.7%) of BD51 as a light yellow solid.
MS (MALDI-TOF): m/z 1,048 [M]$^+$ Preparative Example 2

Synthesis of Compound BD83

3.7 g (yield 32%) of BD83 as a light yellow solid was synthesized in the same manner as in Preparative Example 1, except that 4-bromo-2-fluoroaniline was used instead of 2,4-dibromo-6-fluoroaniline in Preparative Example 1-(1).
MS (MALDI-TOF): m/z 886 [M]$^+$ Preparative Example 3

Synthesis of Compound BD1

1.8 g (yield 29%) of BD1 as a light yellow solid was synthesized in the same manner as in Preparative Example 1, except that 4-fluoroaniline and bromobenzene-d$_5$ were used instead of 4-bis(phenyl-d$_5$)-6-fluoroaniline and 4-bromobiphenyl in Preparative Example 1-(2), respectively.
MS (MALDI-TOF): m/z 582 [M]$^+$ Preparative Example 4

Synthesis of Compound BD39

1.2 g (yield 11%) of BD39 as a light yellow solid was synthesized in the same manner as in Preparative Example 1, except that p-tolylboronic acid was used instead of phenylboronic acid-d$_5$ in Preparative Example 1-(1) and bromobenzene-d$_5$ was used instead of 4-bromobiphenyl in Preparative Example 1-(2).
MS (MALDI-TOF): m/z 942 [M]$^+$ Preparative Example 5

Synthesis of Compound BD78

1.6 g (yield 18%) of BD78 as a light yellow solid was synthesized in the same manner as in Preparative Example 1, except that 4-bromo-2-fluoroaniline was used instead of 2,4-dibromo-6-fluoroaniline in Preparative Example 1-(1) and 1-bromo-4-(trimethylsilyl)benzene was used instead of 4-bromobiphenyl in Preparative Example 1-(2).
MS (MALDI-TOF): m/z 878 [M]$^+$ Preparative Example 6

Synthesis of Compound BD27

3.1 g (yield 43%) of BD27 as a light yellow solid was synthesized in the same manner as in Preparative Example 1, except that 3-fluoroaniline and bromobenzene-d$_5$ were used instead of 2,4-bis(phenyl-d$_5$)-6-fluoroaniline and 4-bromobiphenyl in Preparative Example 1-(2), respectively.
MS (MALDI-TOF): m/z 582 [M]$^+$ Examples 1-6

Fabrication of Organic Electroluminescent Devices

ITO glass was patterned to have a light-emitting area of 3 mm×3 mm, followed by cleaning. After the patterned ITO glass was mounted in a vacuum chamber, the base pressure was adjusted to 1×10$^{-7}$ torr. A CuPc layer (800 Å) and an α-NPD layer (300 Å) were sequentially formed on the ITO. Thereafter, a layer (250 Å) composed of a mixture of BH1 and BD51 (3%) synthesized in Preparative Example 1-(3) was formed on the α-NPD layer. Then, an Alq$_3$ layer (350 Å), a LiF layer (5 Å) and an Al layer (500 Å) were formed in this order on the BH1/BD51 layer to fabricate an organic electroluminescent device. The luminescent properties of the organic electroluminescent device were measured at 0.4 mA.

The above procedure was repeated except that the compounds synthesized in Preparative Examples 2-6 were used instead of BD51 to fabricate organic electroluminescent devices. The luminescent properties of the organic electroluminescent devices were measured at 0.4 mA.

Comparative Examples 1-2

Organic electroluminescent devices were fabricated in the same manner as in Example 1, except that BD90 (Comparative Example 1) and BD91 (Comparative Example 2) were used instead of BD90. The structures of BD90 and BD91 are as follows.

BD90

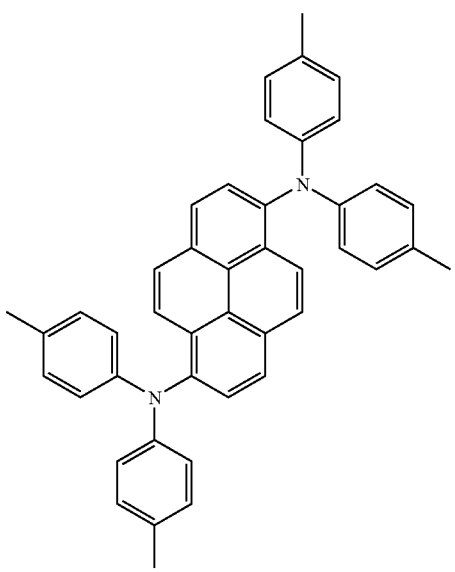

BD91

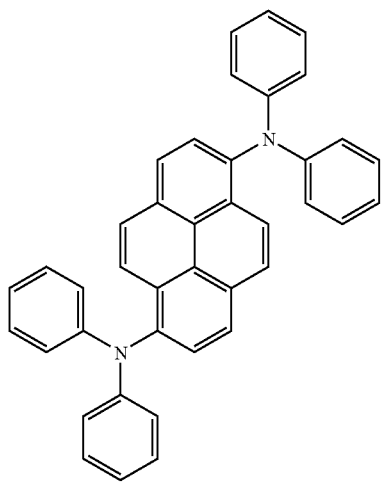

The organic electroluminescent devices fabricated in Examples 1-6 and Comparative Examples 1-2 were tested for voltage, current, luminance, chromaticity coordinates and lifetime. The results are shown in Table 1. T80 indicates the time at which the luminance of each of the devices was decreased to 80% of the initial luminance.

TABLE 1

| | Properties | | | | | |
|---|---|---|---|---|---|---|
| | V | J (mA/cm$^2$) | Cd/m$^2$ | CIEx | CIEy | Life time (T80) |
| Example 1 | 5.5 | 10 | 879 | 0.1317 | 0.1603 | 114 |
| Example 2 | 5.1 | 10 | 852 | 0.1365 | 0.1486 | 148 |
| Example 3 | 5.9 | 10 | 667 | 0.1328 | 0.1297 | 114 |
| Example 4 | 5.1 | 10 | 897 | 0.1326 | 0.1507 | 132 |
| Example 5 | 5.3 | 10 | 708 | 0.1372 | 0.1177 | 96 |
| Example 6 | 6.1 | 10 | 781 | 0.1325 | 0.1443 | 112 |
| Comparative Example 1 | 5.9 | 10 | 652 | 0.1745 | 0.2245 | 57 |
| Comparative Example 2 | 6.3 | 10 | 515 | 0.1488 | 0.1655 | 45 |

As can be seen from the results in Table 1, the organic electroluminescent devices of Examples 1-6 had better color purity than the devices of Comparative Examples 1-2 using the conventional blue light-emitting compounds. In addition, the devices of Examples 1-6 had longer lifetimes than the devices of Comparative Examples 1-2.

The performance characteristics of the organic electroluminescent devices of Examples 1-6 are shown in FIGS. 2 through 5. Specifically, FIGS. 2 and 3 graphically show changes in the luminance of the devices of Examples 1-6 and Comparative Examples 1-2 as a function of time, and FIGS. 4 and 5 graphically show changes in the relative luminance (T80) of the devices of Examples 1-6 and Comparative Examples 1-2 as a function of current density.

As is apparent from the foregoing, the organic electroluminescent device of the present invention, which comprises an organic material layer containing the compound of Formula 1, has high color purity of blue light and shows excellent life characteristics. Therefore, the organic electroluminescent device of the present invention is suitable for use in various applications, such as displays and lighting systems.

What is claimed is:

1. A pyrene compound of Formula 1:

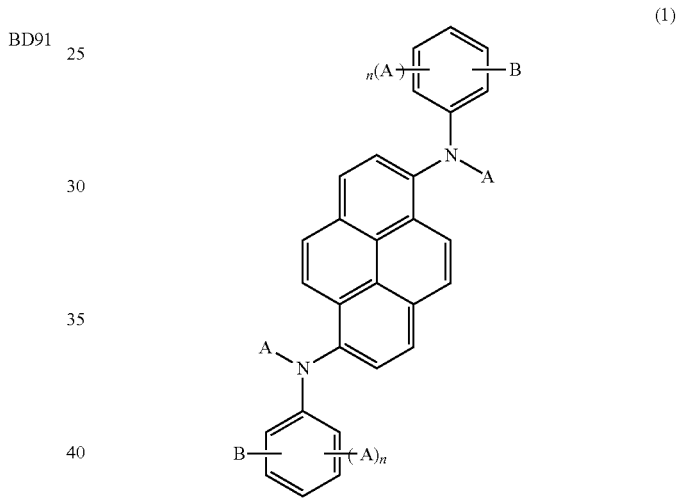

(1)

wherein n is 1 or 2, and A is independently selected from substituted or unsubstituted $C_6$-$C_{40}$ aryl, or substituted or unsubstituted $C_1$-$C_{20}$ alkyl provide that at least one A is

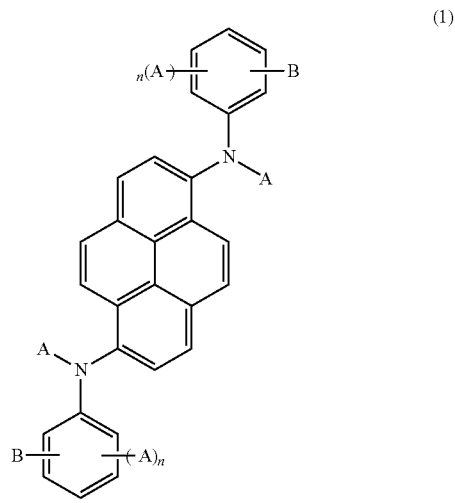

(1)

A is same or different if A is plural, and B is a halogen atom.

2. The pyrene compound of claim 1, wherein the pyrene compound is selected from the group consisting of the compounds represented by following Formulas:
BD37
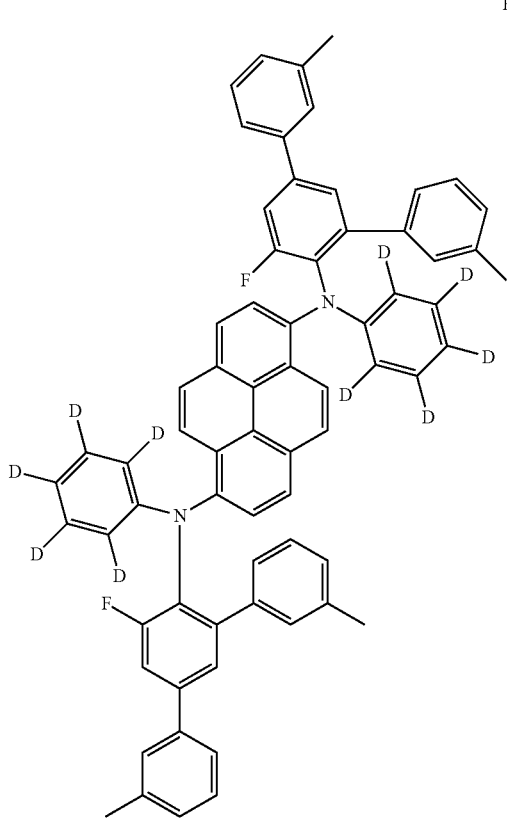
BD38
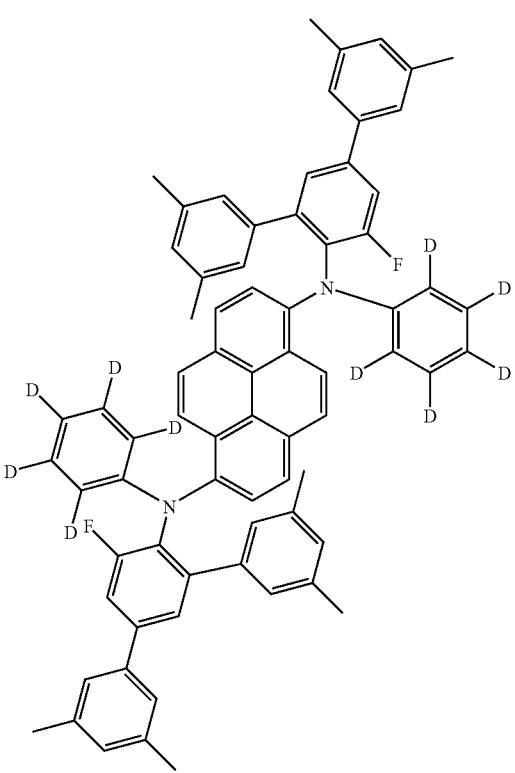
-continued
BD39
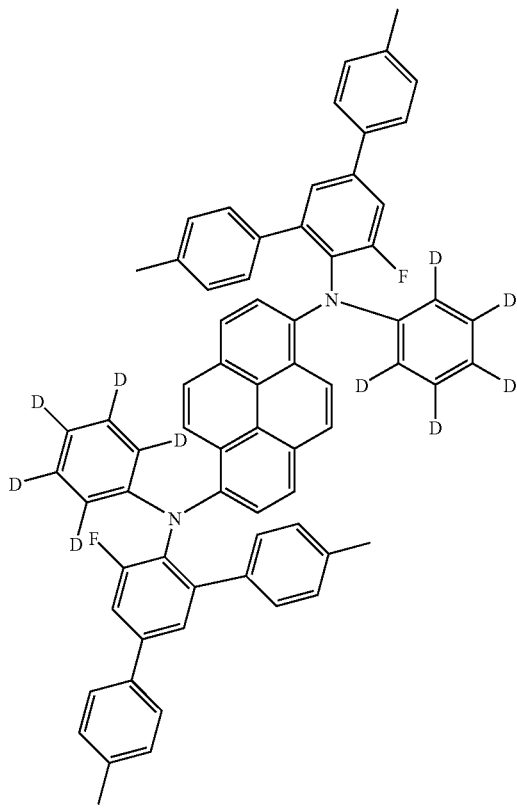
BD40
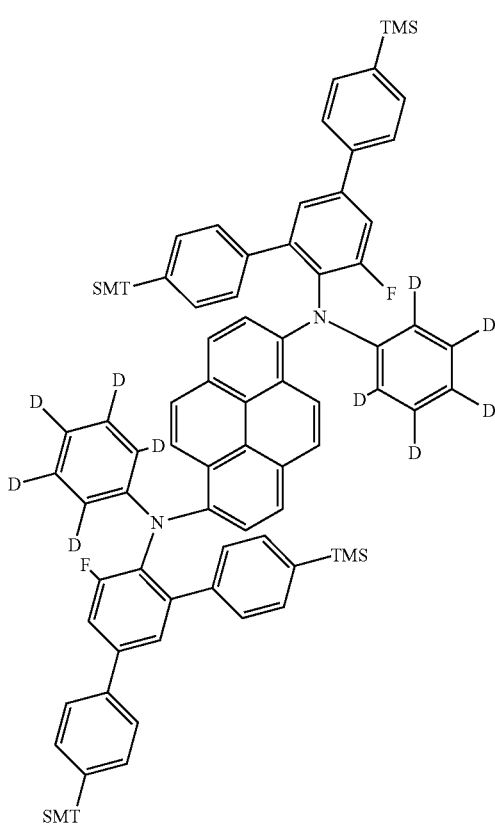

71
-continued
BD43
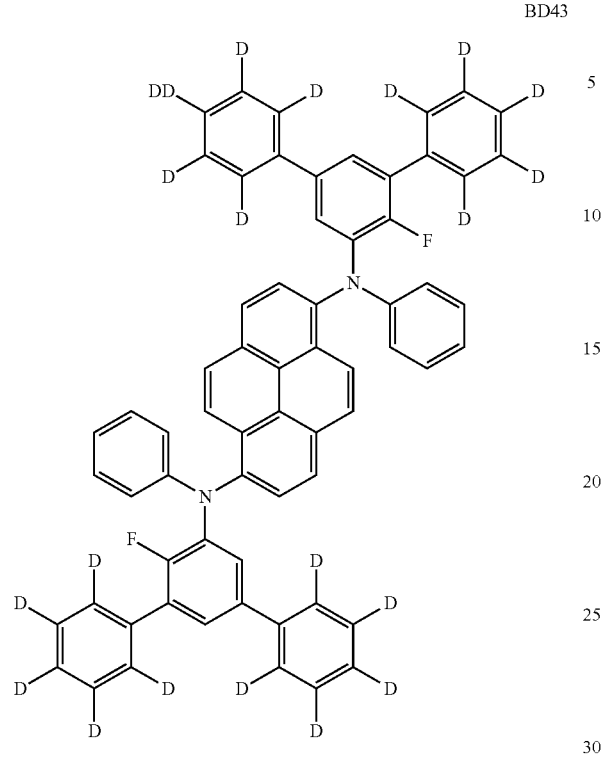
BD44
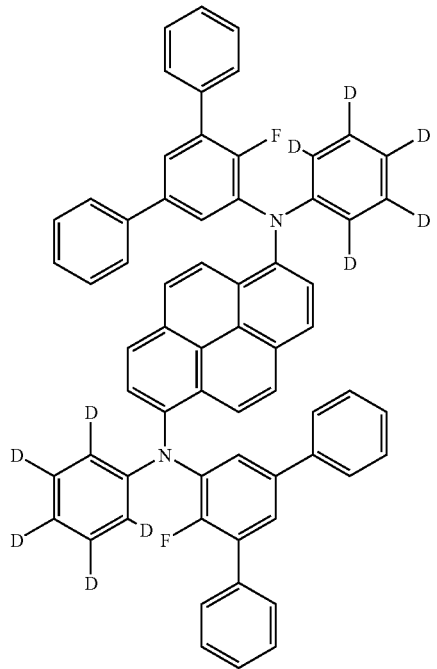
72
-continued
BD45
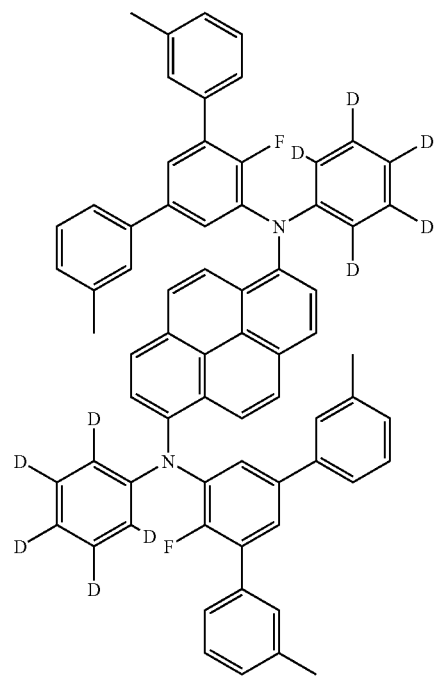
BD46
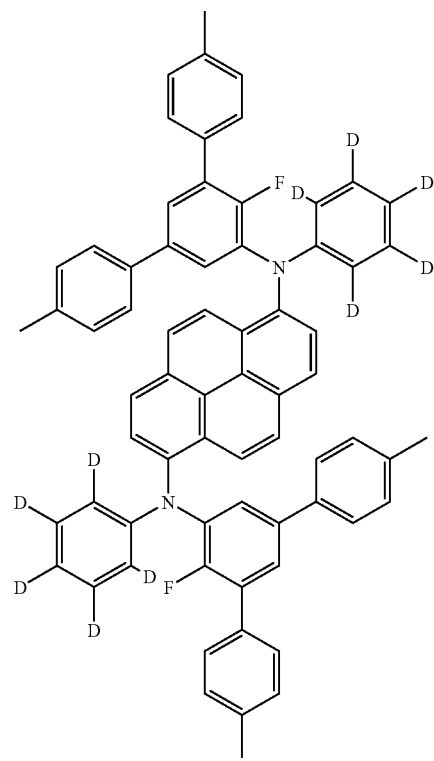

BD47
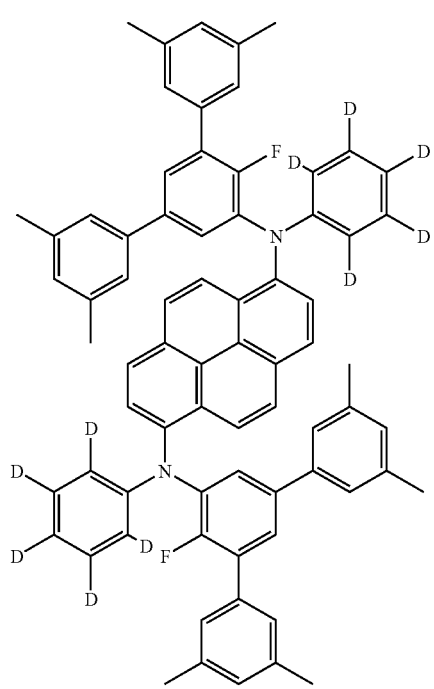
BD49
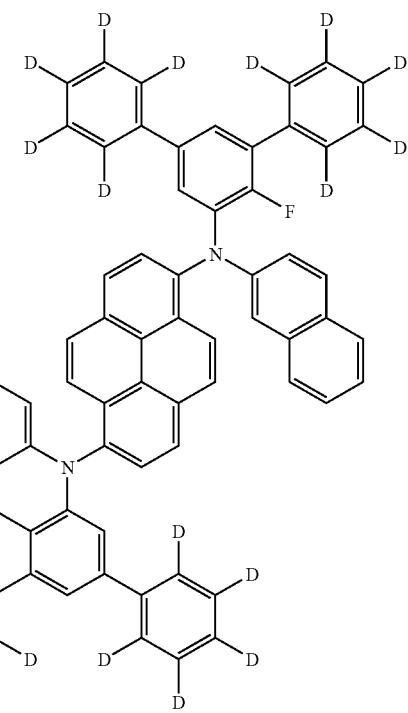
BD48
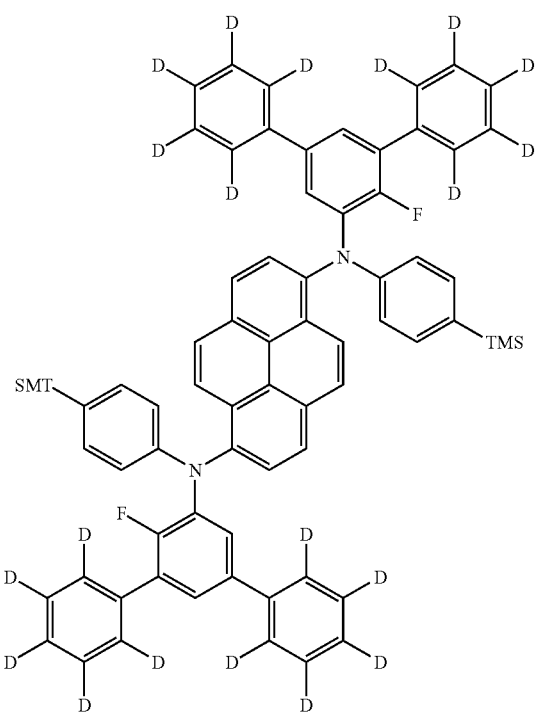
BD50
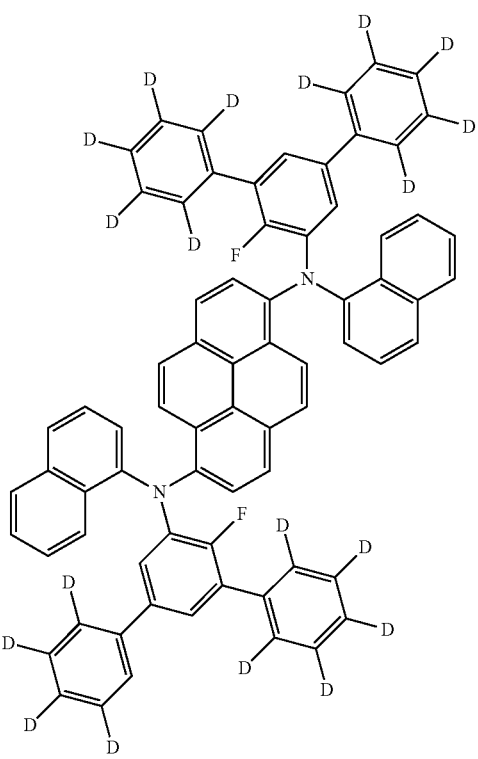

BD51
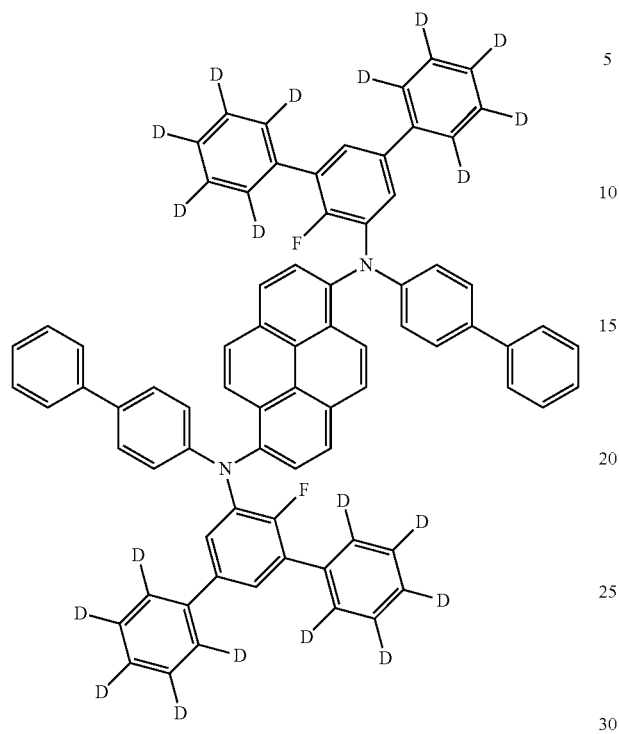
BD54
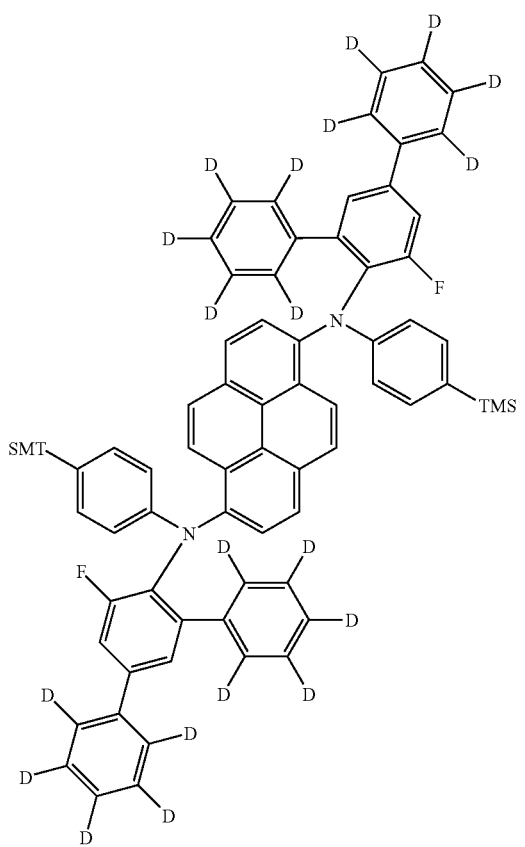
BD55
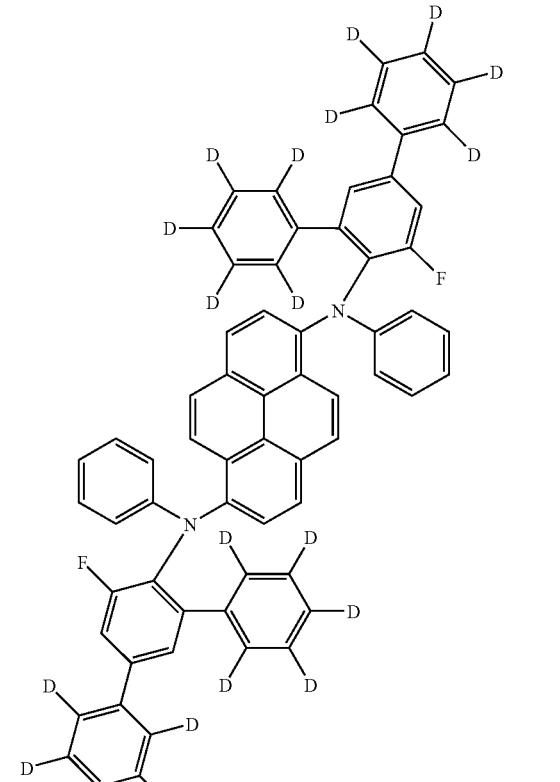
BD56
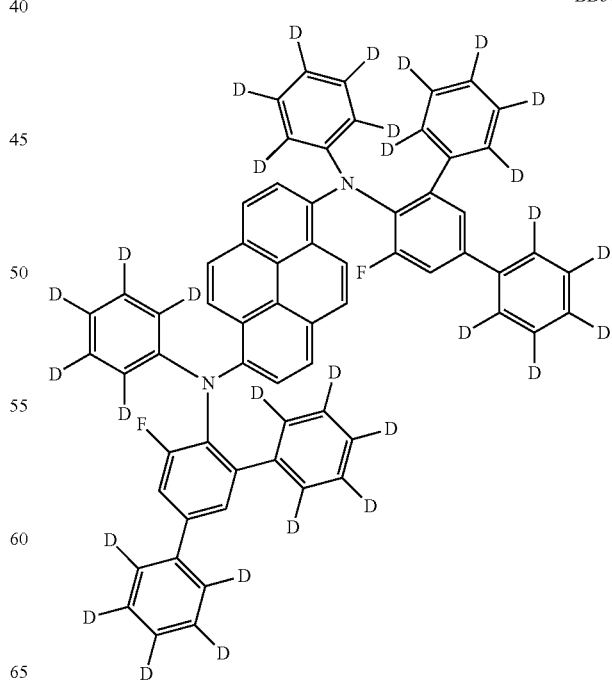

-continued
BD57
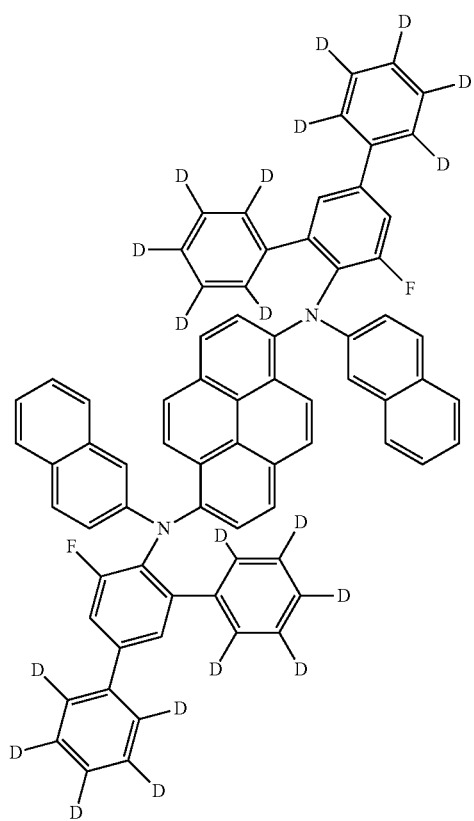
BD58
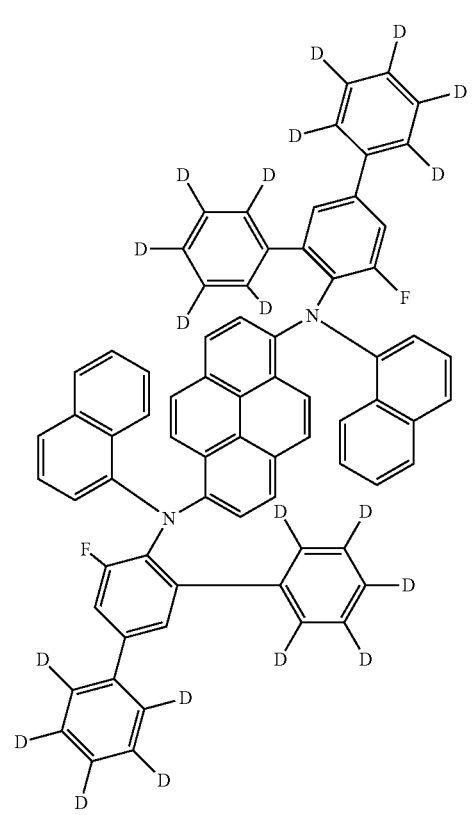
-continued
BD59
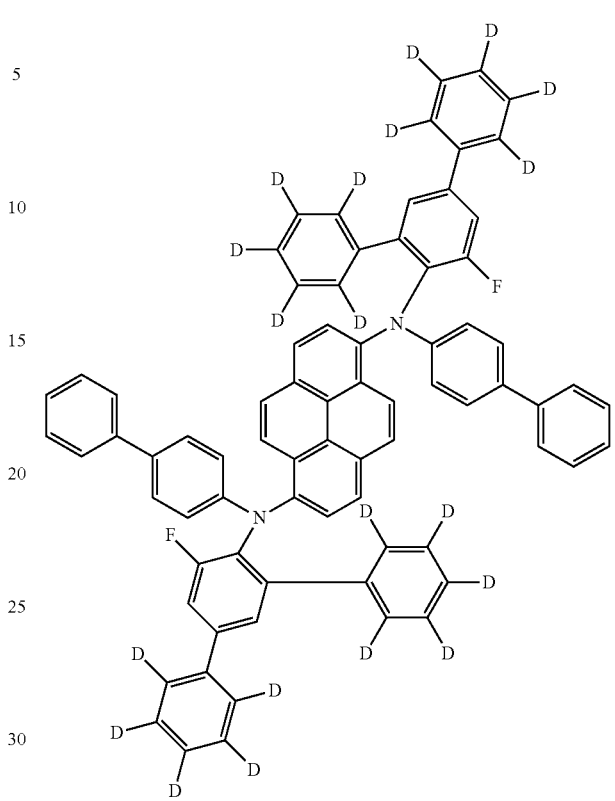
BD60
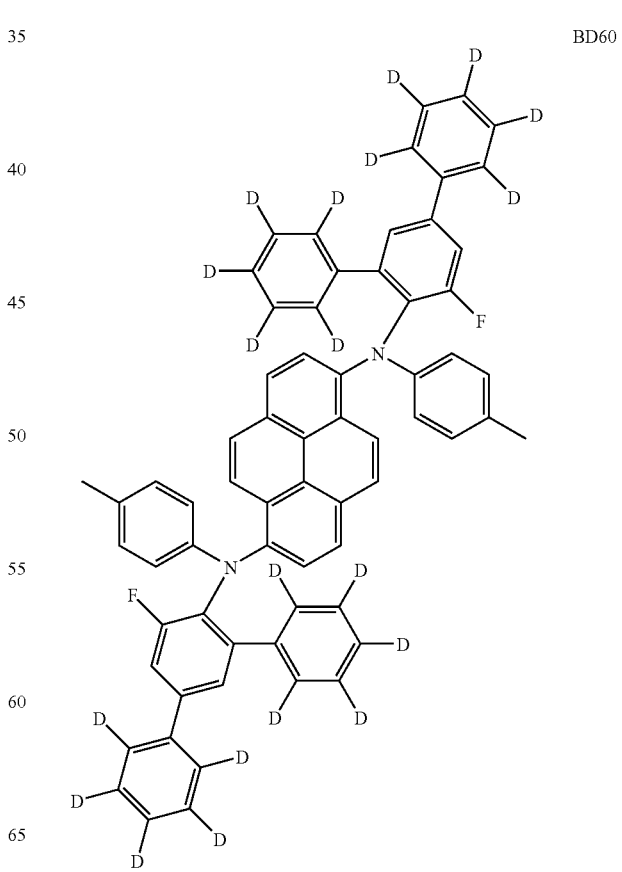

79
-continued
BD61
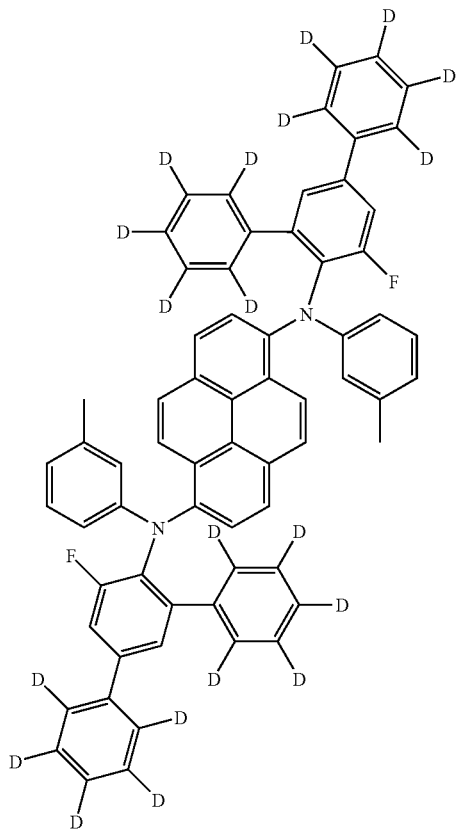
BD62
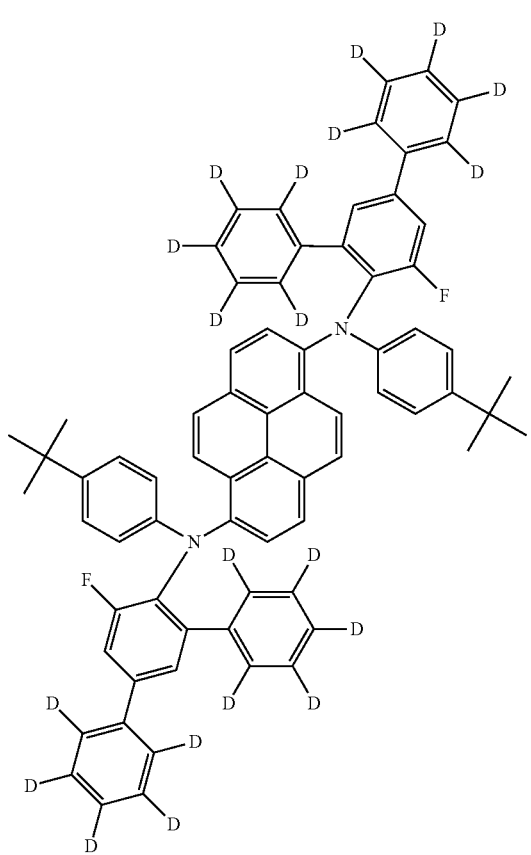
80
-continued
BD78
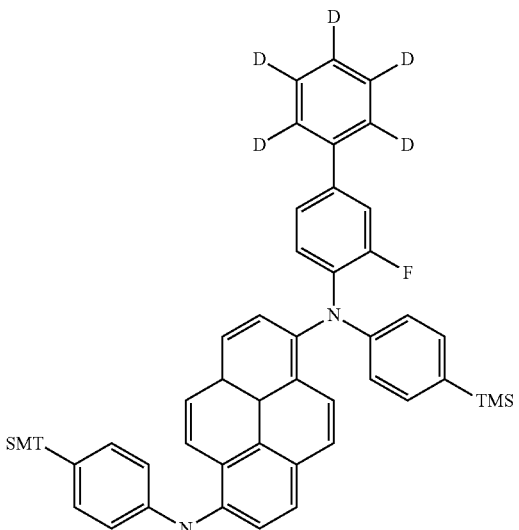
BD79
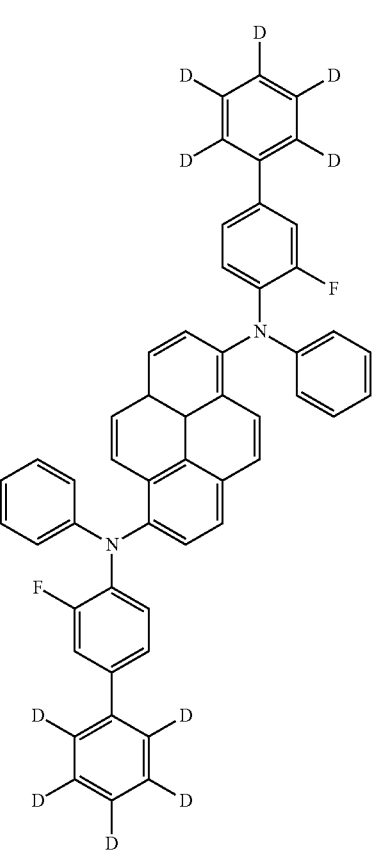

-continued

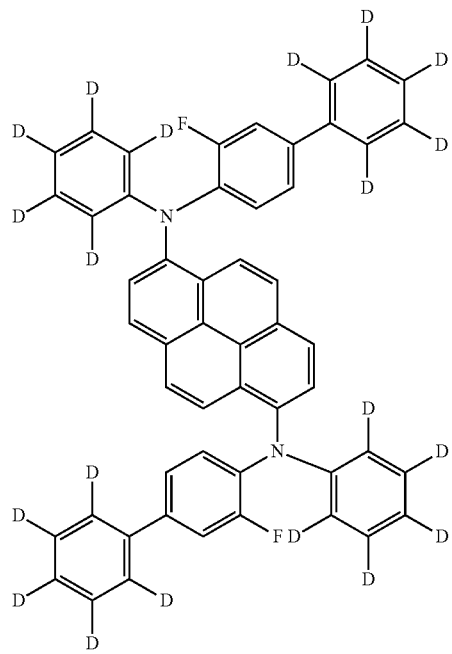
BD80

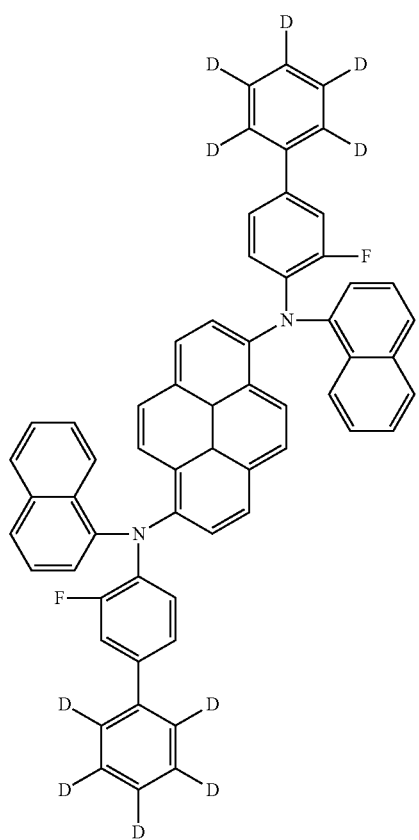
BD82

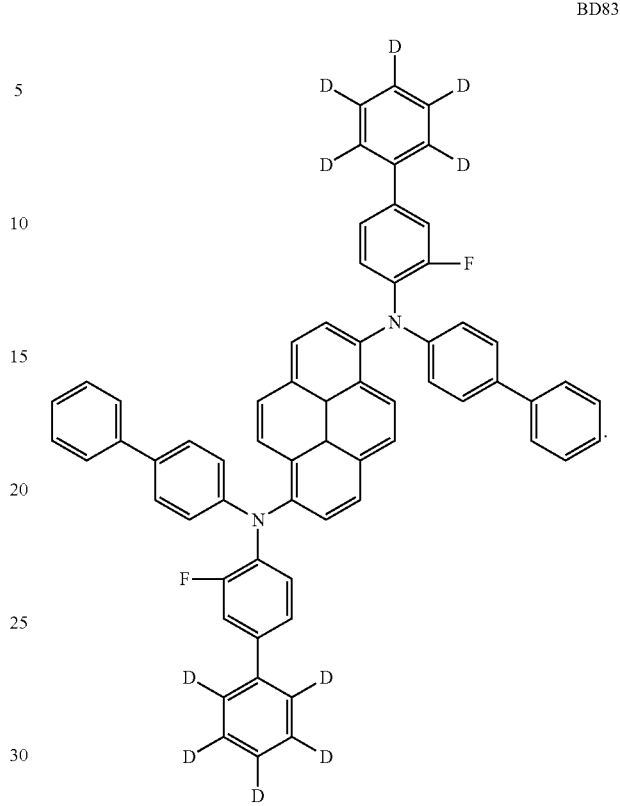
BD83

3. An organic electroluminescent device comprising an anode, a cathode and a layer interposed between the two electrodes wherein the layer contains the pyrene compound of claim 1.

4. The organic electroluminescent device of claim 3, wherein the layer containing the pyrene compound is a light emitting layer.

5. The organic electroluminescent device of claim 4, further comprising, between the anode and the cathode, one or more layers selected from the group consisting of a hole injecting layer, a hole transport layer, an electron blocking layer, a hole blocking layer, an electron transport layer and an electron injecting layer.

6. The organic electroluminescent device of claim 5, wherein at least one layer of the hole injecting layer, the hole transport layer, the light emitting layer, the electron blocking layer, the hole blocking layer, the electron transport layer and the electron injecting layer is formed by solution processing.

7. The organic electroluminescent device of claim 4, wherein the light emitting layer further contains one or more compounds selected from the following compounds BH1 to BH39:

BH01
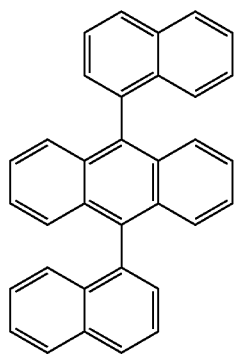
BH02
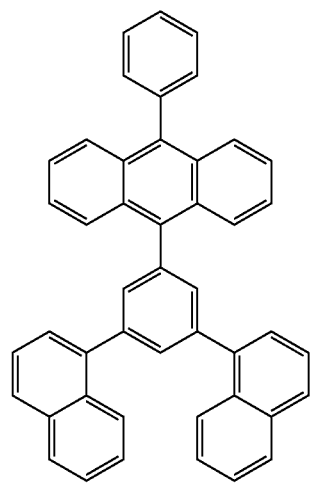
BH03
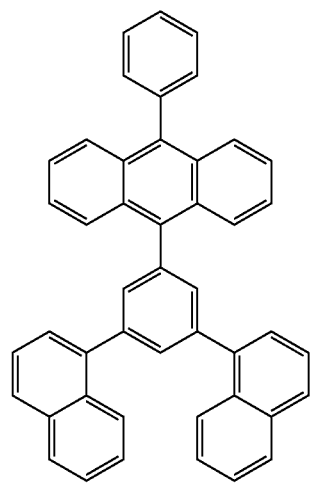
BH04
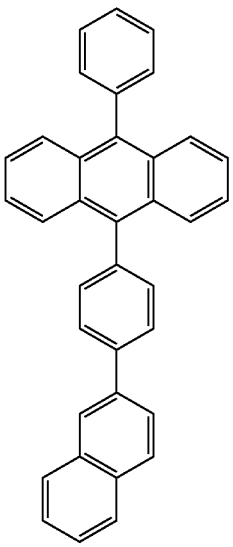
BH05
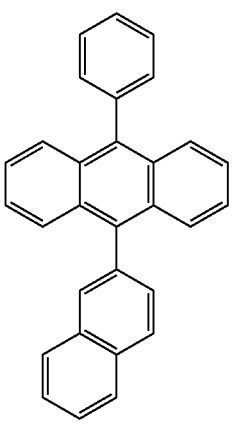
BH06
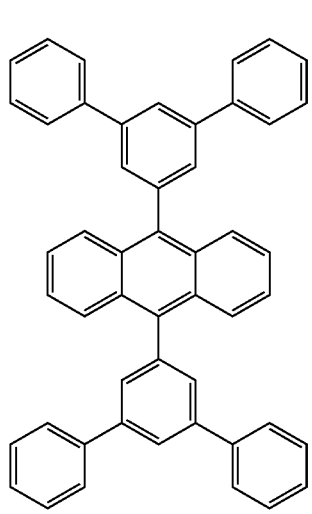

BH07
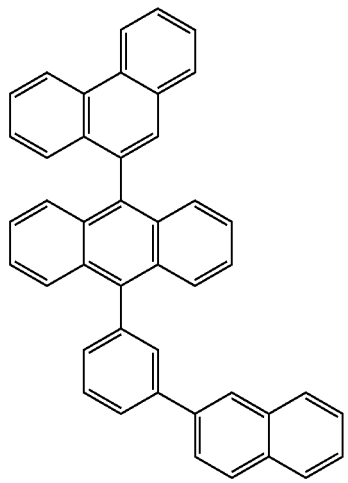
BH08
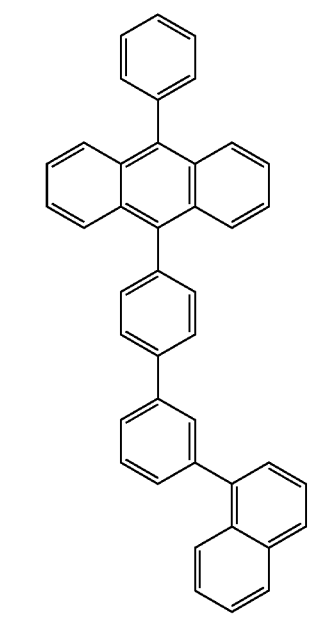
BH09
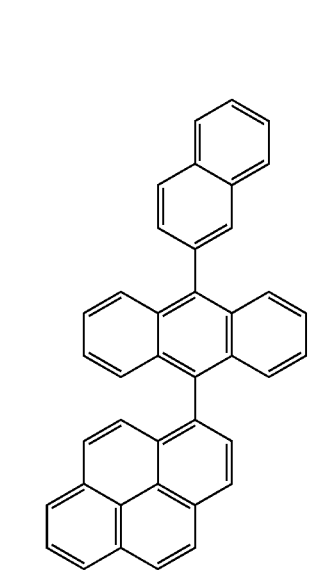
BH10
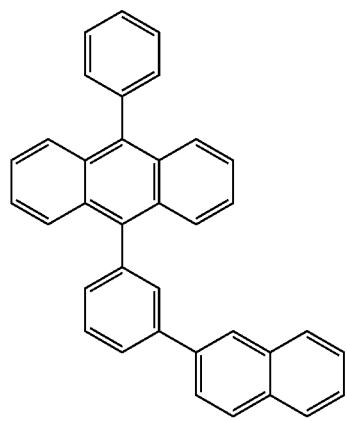
BH11
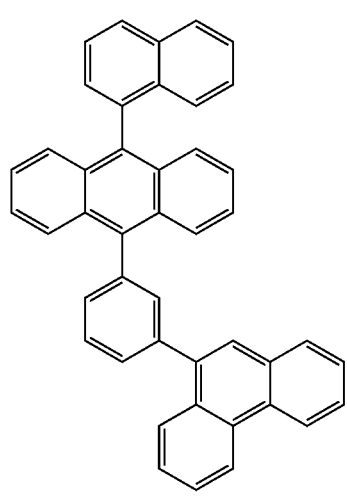
BH12
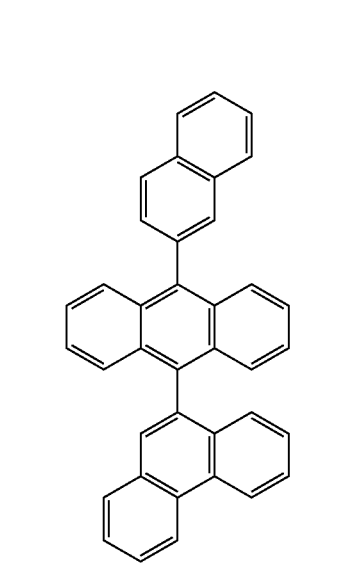

-continued
BH13
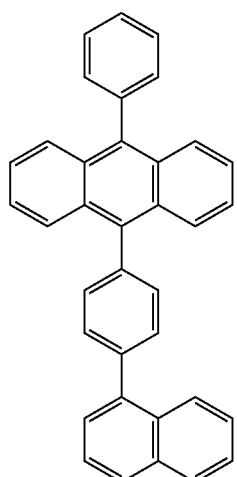
BH14
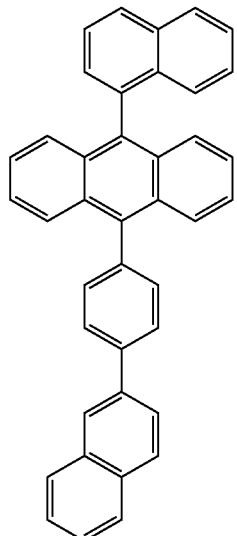
BH15
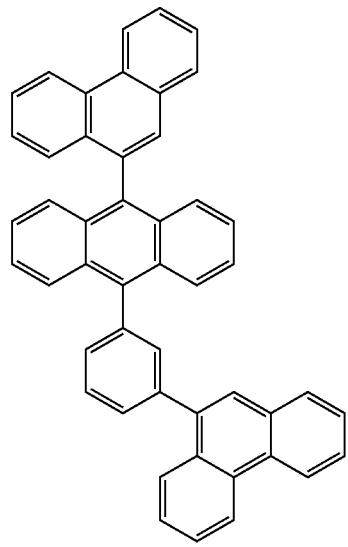
-continued
BH16
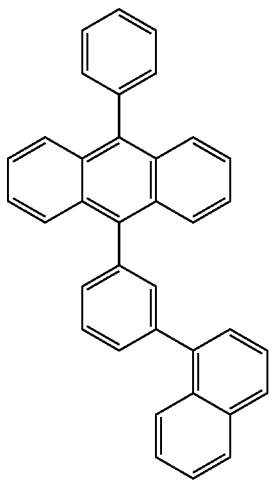
BH17
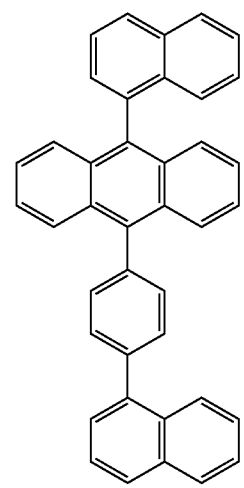
BH18
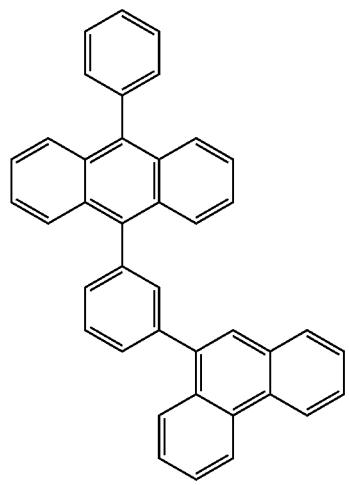

BH19
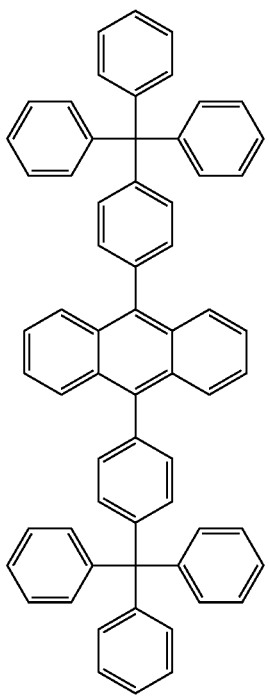
BH21
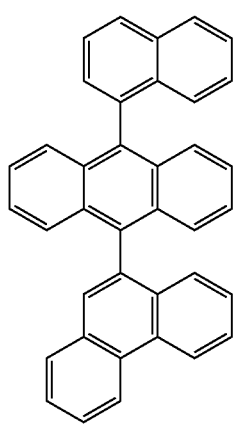
BH22
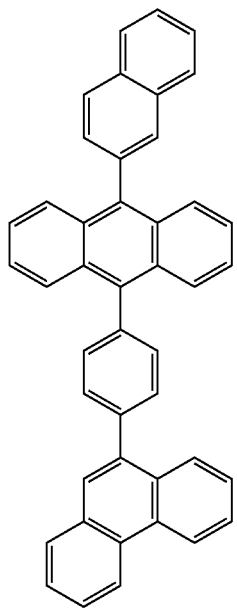
BH20
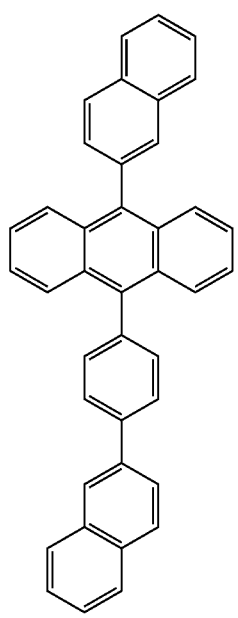
BH23
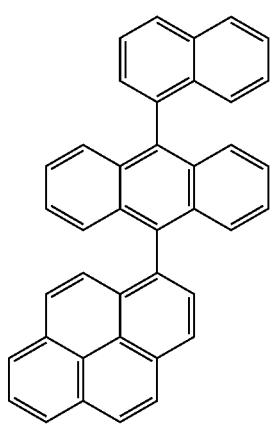

BH24
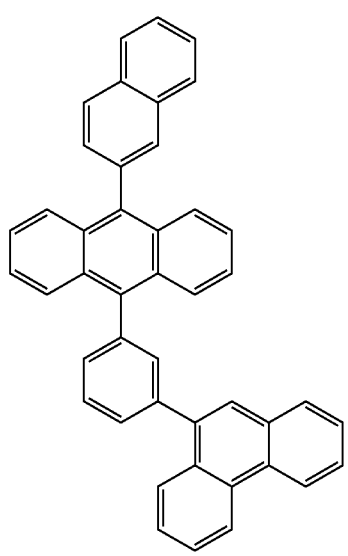
BH25
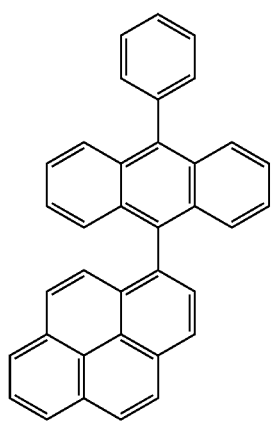
BH26
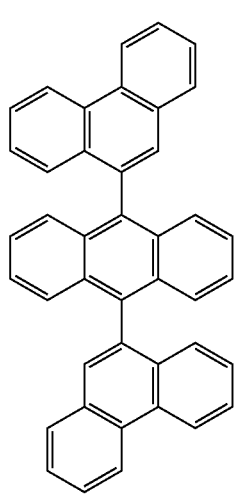
BH27
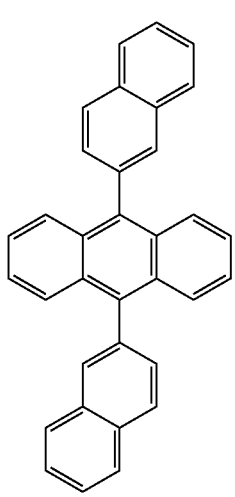
BH28
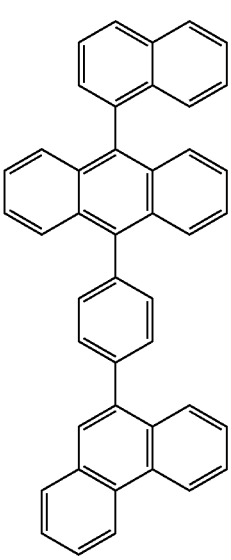
BH29
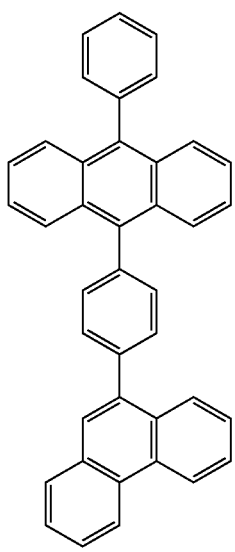

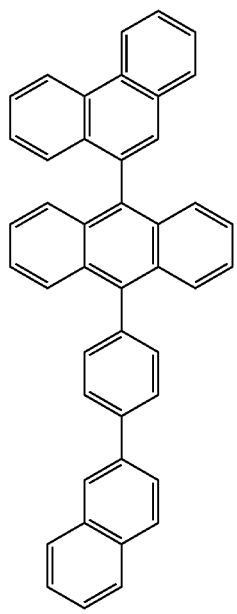
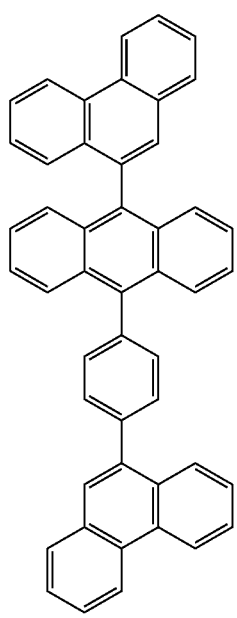
BH30
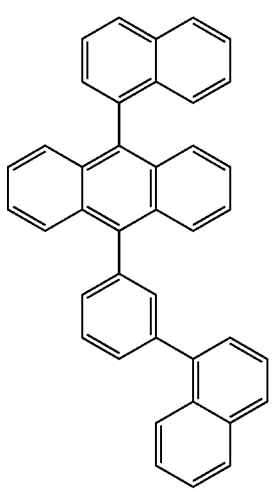
BH32
BH33
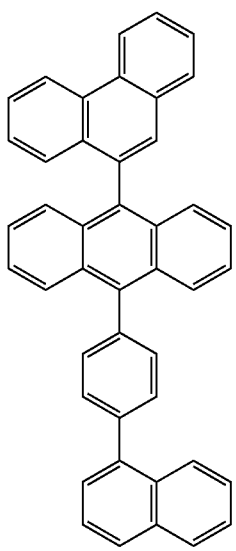
BH34
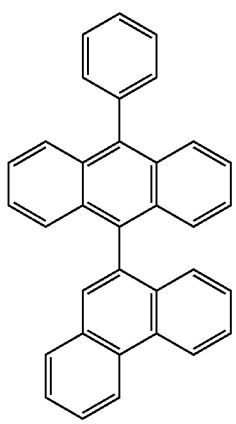
BH31

BH35
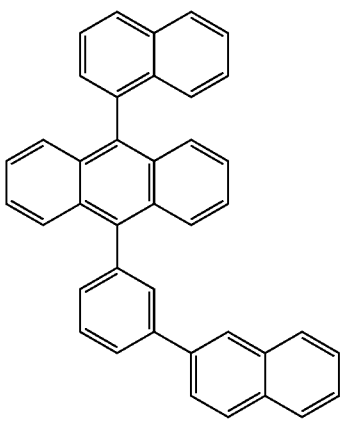
BH36
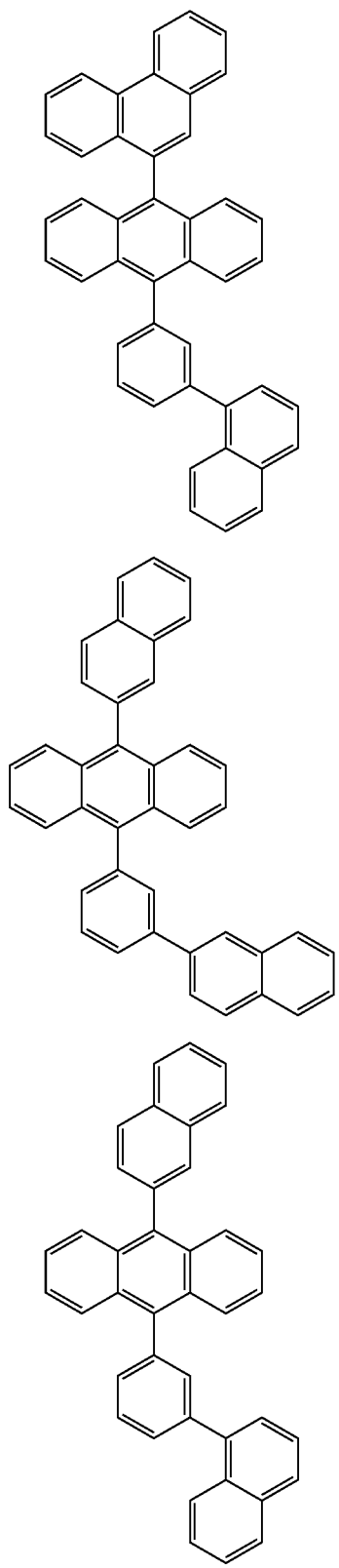
BH37
BH38
BH39
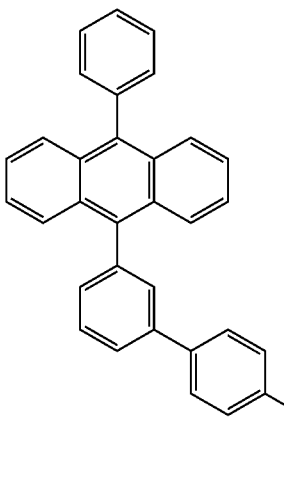
8. The organic electroluminescent device of claim 3, wherein the organic electroluminescent device is used for the manufacture of a display, a display device, a monochromatic lighting device or a white lighting device.
* * * * *

UNITED STATES PATENT AND TRADEMARK OFFICE
CERTIFICATE OF CORRECTION

PATENT NO. : 8,541,113 B2
APPLICATION NO. : 12/545301
DATED : September 24, 2013
INVENTOR(S) : Je et al.

Page 1 of 1

It is certified that error appears in the above-identified patent and that said Letters Patent is hereby corrected as shown below:

In the claims

Column 68,

Lines 47-66, the drawing should appear as follows:

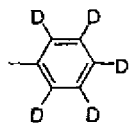

Signed and Sealed this
Thirty-first Day of December, 2013

Margaret A. Focarino
*Commissioner for Patents of the United States Patent and Trademark Office*